(12) United States Patent
Irrgang et al.

(10) Patent No.: US 11,758,263 B2
(45) Date of Patent: Sep. 12, 2023

(54) SYSTEMS, DEVICES, AND METHODS FOR IMAGING AND MEASUREMENT USING A STEREOSCOPIC CAMERA SYSTEM

(71) Applicant: MOLECULIGHT INC., Toronto (CA)

(72) Inventors: Claudio Irrgang, Brampton (CA); Steven P. Meyer, Toronto (CA); Desmond Hirson, North York (CA)

(73) Assignee: MOLECULIGHT, INC., Toronto (CA)

( * ) Notice: Subject to any disclaimer, the term of this patent is extended or adjusted under 35 U.S.C. 154(b) by 13 days.

(21) Appl. No.: 17/410,040

(22) Filed: Aug. 24, 2021

(65) Prior Publication Data

US 2023/0067762 A1    Mar. 2, 2023

(51) Int. Cl.
| | | |
|---|---|---|
| *H04N 13/106* | (2018.01) | |
| *H04N 13/156* | (2018.01) | |
| *H04N 13/239* | (2018.01) | |

(Continued)

(52) U.S. Cl.
CPC .......... *H04N 23/631* (2023.01); *G06T 7/0012* (2013.01); *G06T 7/337* (2017.01); *G06T 7/85* (2017.01); *H04N 13/128* (2018.05); *H04N 13/156* (2018.05); *H04N 13/239* (2018.05); *H04N 13/254* (2018.05); *H04N 13/296* (2018.05); *H04N 23/64* (2023.01); *G06T 2207/10064* (2013.01); *G06T 2207/30088* (2013.01); *H04N 2013/0081* (2013.01)

(58) Field of Classification Search
CPC ... H04N 5/232933; G06T 7/0012; G06T 7/337; G06T 7/85; H04N 5/23222; H04N 13/128; H04N 13/156; H04N 13/239; H04N 13/254; H04N 13/296; G06T 2207/10064; G06T 2207/30088; H04N 2013/0081

USPC ............................................................ 348/47
See application file for complete search history.

(56) References Cited

U.S. PATENT DOCUMENTS

| | | | | |
|---|---|---|---|---|
| 2,918,855 | A | 12/1959 | Wilkenson | |
| 9,426,450 | B1* | 8/2016 | Zhang et al. | ............ G02B 3/12 |

(Continued)

FOREIGN PATENT DOCUMENTS

| | | |
|---|---|---|
| CA | 3127048 A1 | 7/2020 |
| JP | 4420011 B2 | 2/2010 |

(Continued)

OTHER PUBLICATIONS

International Search Report and Written Opinion dated Nov. 24, 2022 for PCT Application No. PCT/CA2022/051274, 9 pages.

*Primary Examiner* — Susan E. Torgerson
(74) *Attorney, Agent, or Firm* — Jones Robb, PLLC

(57) ABSTRACT

A portable, handheld system for target measurement is provided. The system comprises an imaging assembly comprising first and second camera sensors, separated from one another by a fixed separation distance; and a processor operably coupled to the imaging assembly, the processor being configured to: activate the imaging assembly to capture a primary image of the target with the first camera sensor and to capture a secondary image of the target with the second camera sensor, wherein the target is in a field of view of each of the first and second camera sensors; analyze the captured primary and secondary images to determine a pixel shift value for the target; calculate a parallax value between the primary and secondary images using the determined pixel shift value; compute measurement data related to the target based on the calculated parallax value; and output the measurement data to a display of the imaging system.

40 Claims, 16 Drawing Sheets

(51) Int. Cl.
*H04N 13/254* (2018.01)
*G06T 7/80* (2017.01)
*G06T 7/00* (2017.01)
*H04N 23/63* (2023.01)
*H04N 13/296* (2018.01)
*H04N 13/128* (2018.01)
*G06T 7/33* (2017.01)
*H04N 23/60* (2023.01)
*H04N 13/00* (2018.01)

(56) References Cited

U.S. PATENT DOCUMENTS

| | | | |
|---|---|---|---|
| 9,861,285 | B2 | 1/2018 | Fright et al. |
| 2012/0035469 | A1* | 2/2012 | Whelan et al. ........ A61B 5/445 600/425 |
| 2012/0281087 | A1 | 11/2012 | Kruse |
| 2017/0236281 | A1* | 8/2017 | Dacosta ............. A61B 5/0071 382/128 |
| 2018/0027994 | A1 | 2/2018 | Bacallao et al. |
| 2018/0082441 | A1* | 3/2018 | Kim et al. ............... G06T 7/85 |
| 2018/0214071 | A1 | 8/2018 | Fright et al. |
| 2019/0192874 | A1* | 6/2019 | Shukla .................. A61B 34/25 |
| 2020/0193597 | A1* | 6/2020 | Fan et al. ............ A61B 5/7275 |

FOREIGN PATENT DOCUMENTS

| | | | |
|---|---|---|---|
| WO | 2008130907 | A1 | 10/2008 |
| WO | 2011118839 | A1 | 9/2011 |
| WO | 2019148265 | A1 | 8/2019 |
| WO | 2020014779 | A1 | 1/2020 |

\* cited by examiner

SYSTEMS, DEVICES, AND METHODS FOR IMAGING AND MEASUREMENT USING A STEREOSCOPIC CAMERA SYSTEM

TECHNICAL FIELD

A system and method for imaging and measurement without fiducial markers or other external or artificial fixed reference points is disclosed. In particular, the system and method may utilize a stereoscopic camera system to capture images to identify characteristics related to a target. In various applications, for example, the target may be a wound and the system and method may be used to determine the wound's size, area, three-dimensional surface, and other characteristics related to the wound, for both human and animal applications.

BACKGROUND

Wound care is a major clinical challenge. Healing and chronic non-healing wounds are associated with a number of biological tissue changes including inflammation, proliferation, remodeling of connective tissues and, a common major concern, bacterial infection. A proportion of wound infections are not clinically apparent and contribute to the growing economic burden associated with wound care, especially in aging populations. Until recently, the gold-standard of wound assessment included direct visual inspection of a wound site under white light combined with indiscriminate collection of bacterial swabs and tissue biopsies. Such conventional wound assement methods presented various issues including inaccurate measurements of the wound, often resulting in delayed, costly, and insensitive bacteriological results.

Imaging systems have now been developed that can image and measure a wound using, for example, images taken of the wound from a camera on the system. Such systems may then analyze and measure the captured wound images to determine the dimensions and area of the wound itself. To make such a determination, the imaging systems must be given a reference scale, including information regarding the distance between the system's camera and the imaged object (i.e., the wound). In a clinical environment, reference scales for measurement of objects have traditionally been provided via two different methods: (1) a first method that utilizes reference objects (such as fiducial markers or other artificial fixed reference points), and (2) a second method that utilizes a projected light pattern.

In the first method, fiducial elements or markers, such as one or more distinctive stickers or self-reference objects, are placed in a field of view of a camera, for example, on the patient adjacent to the wound, or on an instrument that is utilized during the procedure. This technique is suitable for single-camera devices that use off-the-shelf hardware, such as computing tablets or smartphones, and has been shown to yield generally accurate results in most situations. However, it suffers from various disadvantages. The fiducial elements or markers must be sterile to avoid contamination of the patient, take time to apply and remove, and must be safely discarded after every single use. Additionally, as the distance from the camera to an object, such as a wound, is increased, the fiducial elements or markers appear smaller and therefore are less accurately sized for the same resolution camera, for example, when measuring a large object. It is also not always possible to place fiducial elements or markers in optimum locations for imaging, for example, on large or highly irregular shaped objects, which may lead to inaccurate measurements. For optimal measurements, fiducial elements or markers should be adjacent to the wound plane and parallel to the camera's field of view. Fiducial elements or markers also should not be bent or distorted when placed on the patient. Finally, if the lighting of the fiducial elements or markers is not even or if there are elements in the picture that resemble the fiducial elements or markers, the device may have detection errors. For example, if a shadow falls across one of the fiducial elements or markers, the device may be unable to detect the fiducial element or marker. Or portions of the patient's skin of similar shape and size may confuse the detection of the real fiducial elements or markers.

In the second method, a structured light pattern is projected onto the wound area. This technique offers a way to measure an object, such as a wound, without placement of fiducial elements or markers in the field of view, and the physical contact of fiducial elements or markers with instruments or the object (e.g., the patient). However, the technology required to project a non-dispersing beam pattern is highly specialized and expensive. Furthermore, wounds vary significantly in how they reflect and disperse light, which can lead to errors in the measurement data.

To continue to address the challenges of wound care, it may be desirable to provide a relatively simple, inexpensive system and method for wound imaging and measurement, which may measure the distance between the imaging camera and the object of interest (e.g., the wound), to provide accurate wound measurement data without requiring placement of anything in the field of view, and without any direct contact with the patient's body, thereby reducing the possibility of bacterial or viral contamination of the wound or transfer of bacteria to other objects such as fiducial elements or hands placing the fiducial elements.

Of particular interest in clinical wound imaging and measurement is the need to measure the distance from the imaging camera to the wound in real time to keep the distance within a predetermined range. Prior art systems and devices have addressed this need by employing special "range-finding" electronic components. It may be additionally desirable to provide a system and method that carries out this range-finding requirement without the need for special purpose components.

Clinical analysis using an image system requires good quality images. Images often cannot be retaken at a later time and, of course, images taken at a later time may not provide the same information as the original images. It may be further desirable to provide a system and method that can inform the clinical user when the conditions for capturing good measurement images are in range, thereby increasing the probability that a satisfactory image is captured.

SUMMARY

The present disclosure may solve one or more of the above-mentioned problems and/or may demonstrate one or more of the above-mentioned desirable features. Other features and/or advantages may become apparent from the description that follows.

In accordance with one aspect of the present disclosure, a portable, handheld system for measurement of a target is provided. The system comprises an imaging assembly comprising a first camera sensor and a second camera sensor, the first camera sensor being separated from the second camera sensor by a fixed separation distance; and a processor operably coupled to the imaging assembly, the processor being configured to: activate the imaging assembly to capture a primary image of the target with the first camera sensor and to capture a secondary image of the target with the second camera sensor, wherein the target is in a field of view of each of the first and second camera sensors; analyze the captured primary and secondary images to determine a pixel shift value for the target; calculate a parallax value between the primary image and the secondary image using the determined pixel shift value; compute measurement data related to the target based on the calculated parallax value; and output the measurement data to a display of the imaging system.

In accordance with another aspect of the present disclosure, a method for measurement of a target is provided. The method comprises substantially simultaneously capturing a primary image of the target and a secondary image of the target, wherein the primary image is captured by a first camera sensor of a handheld imaging system and the secondary image of the target is captured by a second camera sensor of the handheld imaging system; on a display screen of the handheld imaging system, defining a contour region of the target within the captured primary image; with a processor of the handheld imaging system: determining a pixel shift value for the target within the contour region by applying a parallax algorithm to shift the secondary image until it exactly overlaps the primary image, calculating a parallax value of the primary image at a center of the contour region using the determined pixel shift value, and computing measurement data related to the target based on the defined contour region and the calculated parallax value; and outputting the measurement data to a display of the handheld imaging system.

BRIEF DESCRIPTION OF DRAWINGS

The present disclosure can be understood from the following detailed description either alone or together with the accompanying drawings. The drawings are included to provide a further understanding and are incorporated in and constitute a part of this specification. The drawings illustrate one or more exemplary embodiments of the present disclosure and together with the description serve to explain various principles and operations.

DETAILED DESCRIPTION

Figure 1:
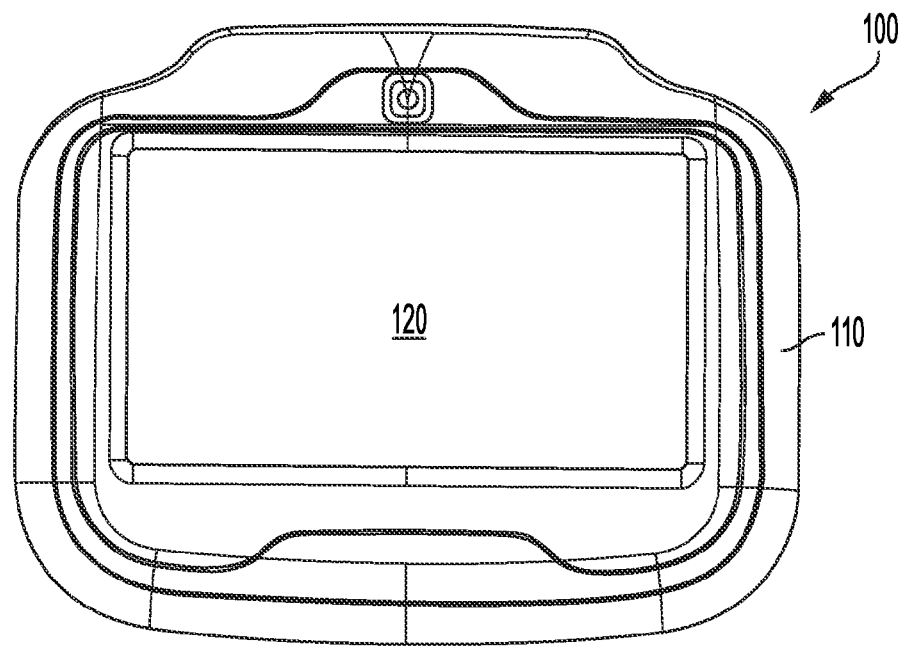
FIG. 1 is a front view of a first embodiment of a handheld imaging system according to the present disclosure.
Figure 2:
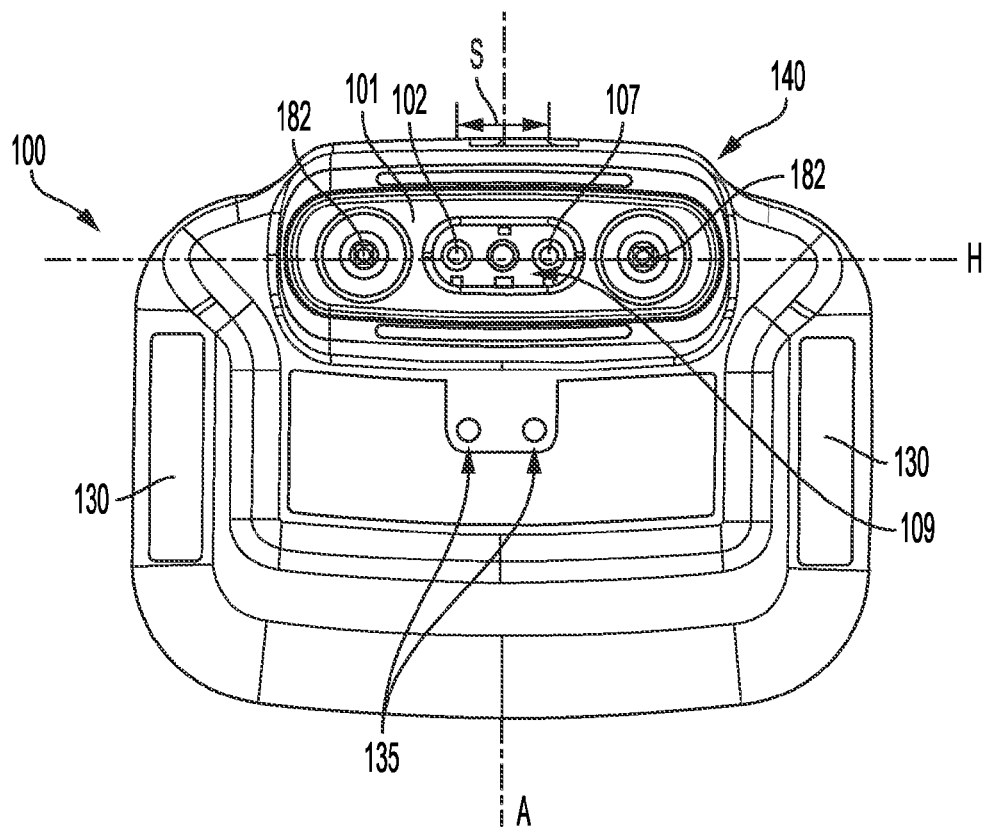
FIG. 2 is a back view of the handheld imaging system of FIG. 1.
Figure 3:
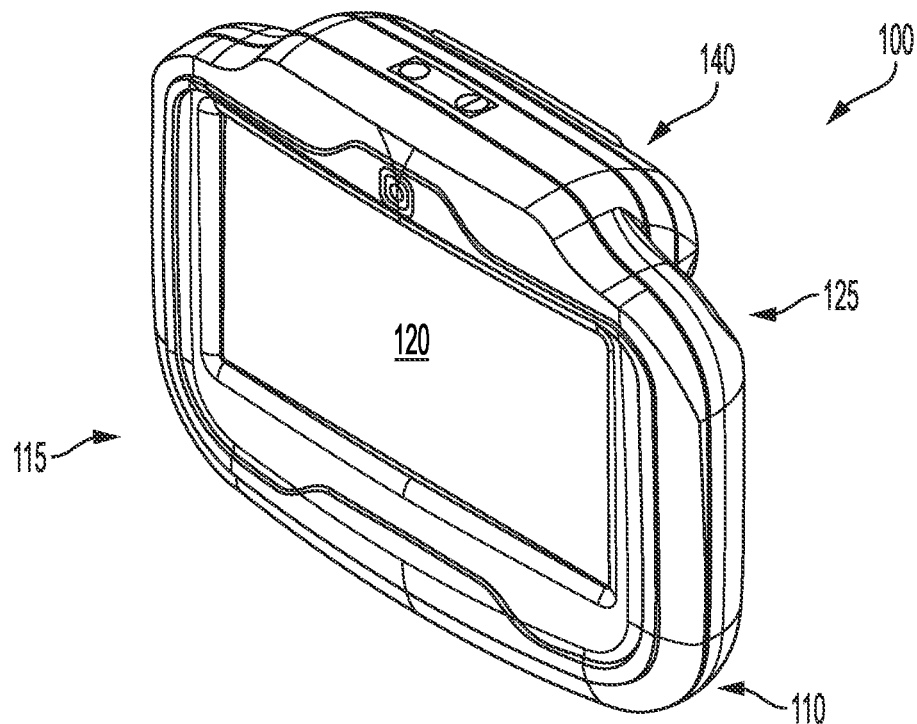
FIG. 3 is a front perspective view of the handheld imaging system of FIG. 1.

Handheld imaging systems can be used to image and measure various characteristics of a target object, such as, for example, a wound, using images taken of the target from one or more cameras on the system. As disclosed, for example, in U.S. Pat. No. 2020/0364862, which is a national stage application of PCT/CA2019/000002, filed internationally on Jan. 15, 2019, which claims benefit to U.S. Provisional Application No. 61/625,611, filed Feb. 2, 2018, the entire content of each of which is incorporated by reference herein, such systems may, for example, analyze pixel data of the captured images to accurately determine characteristics, including, but not limited to, the size (i.e., dimensions), area, depth, and three-dimensional surface profile, of the wound. To conduct pixel data analysis of the captured images, imaging systems must first establish a resolution per pixel of the captured images. This requires creating a reference scale, which is based on the distance between the camera sensor capturing the image and the target being imaged. In a clinical environment, imaging systems have traditionally created a reference scale for measurement of a target using methods which utilize reference objects, such as fiducial elements, markers, or stickers, positioned within the field of view of the camera, next to the target (e.g., affixed to a patient's skin next to the wound or to an instrument utilized during a procedure), or which utilize a complex projected light pattern. Such conventional methods have disadvantages. Methods employing reference objects, for example, require placement of on object within the field of view, either close to or in direct contact with a patient's body (i.e., require affixing stickers to the patient's skin or an instrument that comes into contact with the patient), thereby increasing the possibility of bacterial or viral transfer to or from the wound being imaged. And the technology required to project a non-dispersing beam pattern is highly specialized and expensive, making it generally impractical for most applications.

Systems and methods in accordance with the present disclosure may measure the distance between the imaging camera sensor and a target (e.g., a wound) to provide accurate measurement data without placing anything in the field of view or requiring any direct contact with the target or area around the target (e.g., a patient's body or a medical instrument), thereby increasing the efficiency of the imaging process and reducing the possibility of contamination and error. Systems and methods in accordance with the present disclosure contemplate, for example, employing stereoscopic imaging for range-finding and distance measurement.

In accordance with various exemplary embodiments, systems and methods of the present disclosure may utilize two or more camera sensors with similar characteristics related to focus, field of view, depth of field, white balancing and other standard camera parameters to capture images of a target and can determine an absolute size of the pixels of the captured images using the shift between the images. The amount of shift between the images is also referred to as a pixel shift value (in units of number of pixels), and is proportional to a parallax value (in units of length) of the images. The systems and methods may then utilize the determined pixel size data in the measurement methods disclosed, for example, in U.S. Pat. No. 2020/0364862, the entire contents of which are incorporated by reference herein, to measure almost any kind of wound surface with a high degree of accuracy. Although non-linearities in the manufacture of the camera sensors and various other factors may impact the measurement results, the systems and methods of the present disclosure further contemplate compensating for such differences or imperfections using parameters or corrections derived in a calibration procedure to provide manufacturing calibration coefficients.

In the present application, systems and methods for measurement of a target without fiducial elements or markers, or other artificial fixed reference points are disclosed. One example embodiment of the system is a portable, handheld imaging system that includes an imaging device having two or more cameras (i.e., camera sensors) and a processor coupled to the imaging device for analyzing the images captured from the camera sensors to determine a pixel dimension (i.e., the width of a pixel at the target in mm/pixel) based on the pixel shift between or parallax value of the images. The imaging device, for example, includes a first, primary camera sensor and a second, secondary camera sensor. The first, primary camera sensor and the second, secondary camera sensor may be configured to capture standard, white light (WL) images, fluorescent (FL) images, near infrared (NIR) images, or infrared (IR) images. The sensors may be so configured by use with dedicated filters or filters selectable from a plurality of filters associated with the imaging device (e.g., filter wheel, tunable filters, etc.). Thus, the method disclosed herein may be used to measure features captured in WL, FL, NIR, or IR images. To permit determination of the parallax value of a primary and secondary image (taken, respectively, by the primary and secondary camera sensors), the first camera sensor is separated from the second camera sensor by a predetermined, fixed separation distance.

Figure 21:
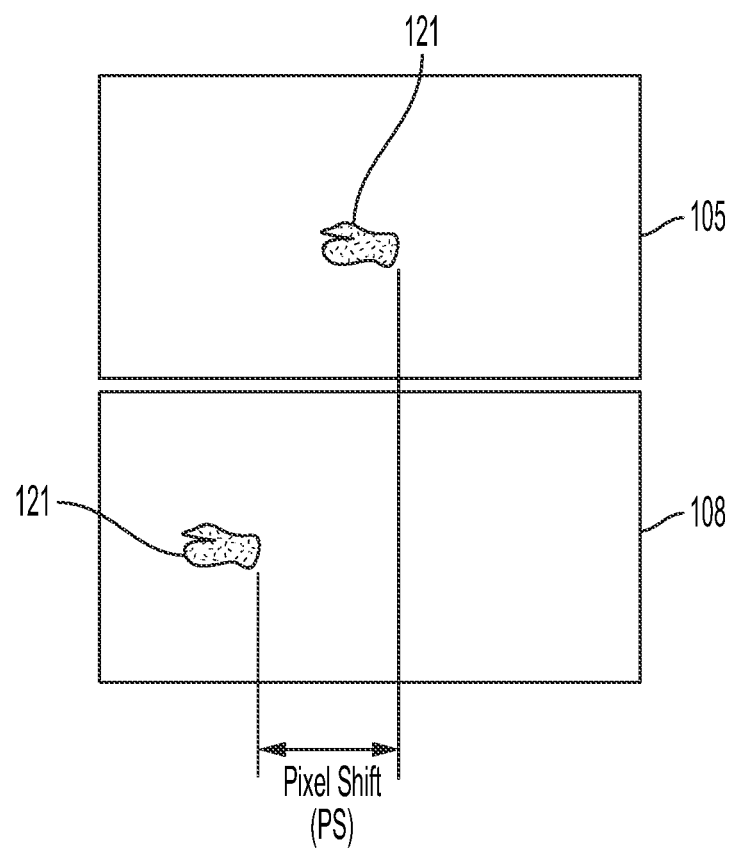
FIG. 21 illustrates an exemplary pixel shift in accordance with the present disclosure.
Figure 22:
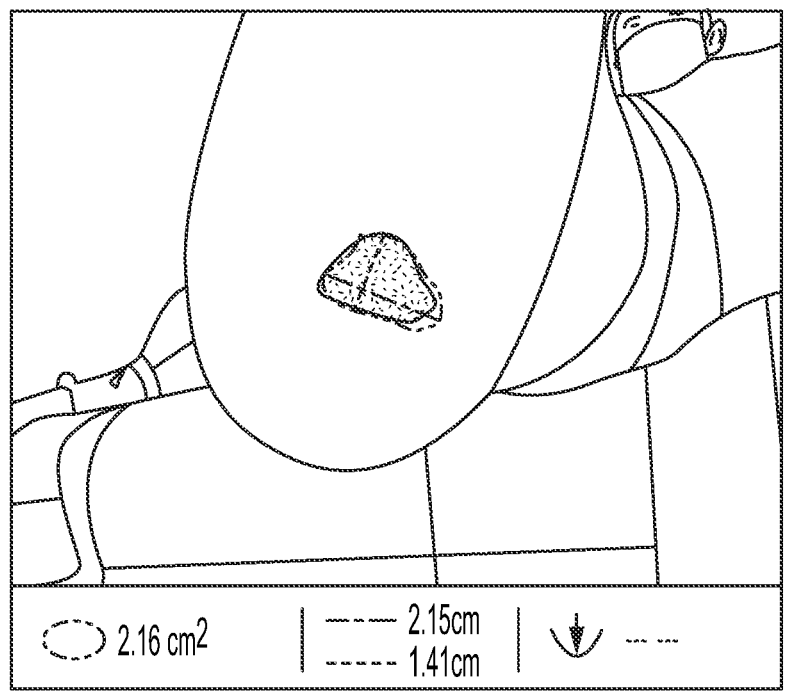
FIG. 22 illustrates an exemplary output of the processor providing measurements of the target.

As will be described in more detail below, the processor is configured to activate the imaging device to substantially simultaneously capture a primary image of the target with the first camera sensor and to capture a secondary image of the target with the second camera sensor and to save the captured images for analysis. To measure the distance between the first camera sensor and a target (e.g., a wound), the processor may, for example, analyze the captured primary and secondary images to determine a parallax value for the target. As illustrated in FIG. 21, for example, a target 121 in a primary image 105 captured by the first camera sensor is seen shifted by a finite number of pixels (a pixel shift value PS) in a secondary image 108 captured by the second camera sensor. The processor may calculate the value PS between the primary image 105 and the secondary image 108 based on the measured amount of parallax. The calculated value PS is then used to determine a pixel size in mm (i.e., a pixel dimension Q as will be described in more detail below) from a calibration table. The calibration table is derived, for example, by measuring a known object in the field of view of both cameras at a specific and predefined depth during a calibration procedure carried out when the device is manufactured. Finally, the determined pixel size can be used to compute and output measurement data related to the target (e.g., wound size and dimensions). In accordance with various embodiments, the measurement data may include one or more of a size, an area, a three-dimensional surface, and/or a depth of the target. An example output of the processor of the device, using the methods disclosed herein to calculate measurement data, is shown in FIG. 22. This output may be, for example, displayed on a display of the handheld imaging system or may be displayed on a display configured to receive transmissions from the handheld imaging system. The Parallax process also provides the distance or range between the cameras and the surface of the wound. In exemplary embodiments, wherein the target is a wound in tissue, the measurement data may include, for example, one or more of a size (e.g., width, length), an area, a three-dimensional surface, and/or a depth of the wound. Although examples discussed herein relate to the target being a wound in tissue, it should be understood that this method of measuring can be applied to any target within the field of view of both the primary and secondary camera sensors.

In various embodiments, for example, the handheld imaging system can include a memory. The memory includes components configured to store and/or retrieve information. In some examples, the memory may be or include one or more storage elements such as Random Access Memory (RAM), Read-Only Memory (ROM), memory circuit, optical storage drives and/or disks, magnetic storage drives and/or tapes, hard disks, flash memory, removable storage media, and the like. The memory can store software which can be used in operation of the imaging system and implementation of the algorithms disclosed herein. Software can include computer programs, firmware, or some other form of machine-readable instructions, including an operating system, utilities, drivers, network interfaces, applications, and the like.

The processor may include, for example, a microprocessor or other circuitry to control other elements of the imaging device, to process instructions retrieved from the storage element or other sources, to execute software instructions to perform various method operations (including but not limited to those described in the present disclosure, to apply signal processing and/or machine learning algorithms to analyze data, to perform calculations and/or predictions, and the like. In some examples, the processor may be or include one or more central processing units (CPUs), arithmetic logic units (ALUs), floating-point units (FPUs), or other microcontrollers.

Individual components of the imaging system may be implemented via dedicated hardware components, by software components, by firmware, or by combinations thereof. Hardware components may include dedicated circuits such as application-specific integrated circuits (ASICs), field-programmable gate arrays (FPGAs), and the like. Software components may include software modules stored in memory, instructions stored on a non-transitory computer readable medium (e.g., internal memory or an external memory) and executed by a processor (e.g., a controller), remote instructions received from an external source (e.g., via a communication circuitry), and the like.

The exemplary systems and methods described herein can be performed, for example, under the control of the processor executing computer-readable codes embodied on a computer-readable recording medium or communication signals transmitted through a transitory medium. The computer-readable recording medium is any data storage device that can store data readable by a processing system, and includes both volatile and nonvolatile media, removable and non-removable media, and contemplates media readable by a database, a computer, and various other network devices. Examples of the computer-readable recording medium include, but are not limited to, read-only memory (ROM), random-access memory (RAM), erasable electrically programmable ROM (EEPROM), flash memory or other memory technology, holographic media or other optical disc storage, magnetic storage including magnetic tape and magnetic disk, and solid-state storage devices.

In accordance with one aspect of the present disclosure, the imaging system includes first and second cameras for taking standard white light (WL) images as well as images taken under specific lighting at different wavelengths. The first and second cameras are operably connected to a computer, which includes a memory and other components configured to execute the methods described herein. The imaging system may include various other components that will permit imaging using various light sources including fluorescent, infrared, and/or white light sources. Various components and systems which may be incorporated into an imaging system as contemplated herein will be described in detail below. It should be understood that any imaging system comprising the necessary components to execute the operations and methods described herein falls within the scope of the present disclosure. Further, although the use of the imaging system is generally described in relation to imaging wounds, use of the disclosed systems and methods are not limited to imaging and measurements of wounds and, instead, are useful in imaging and measuring many different types of targets.

The various structural components of the imaging device and the form factor in which the components are embodied may vary greatly from one imaging device to another. In accordance with the present disclosure, an imaging device configured to practice the methods disclosed herein includes a primary camera (camera sensor) and a secondary camera (camera sensor) fixed in position relative to each other and operably connected to a computer device having a memory and a processor. The imaging device may further include other components selected from those described in the section below entitled "Example Imaging Systems" or those known in the art.

Example Embodiment

Figure 5:
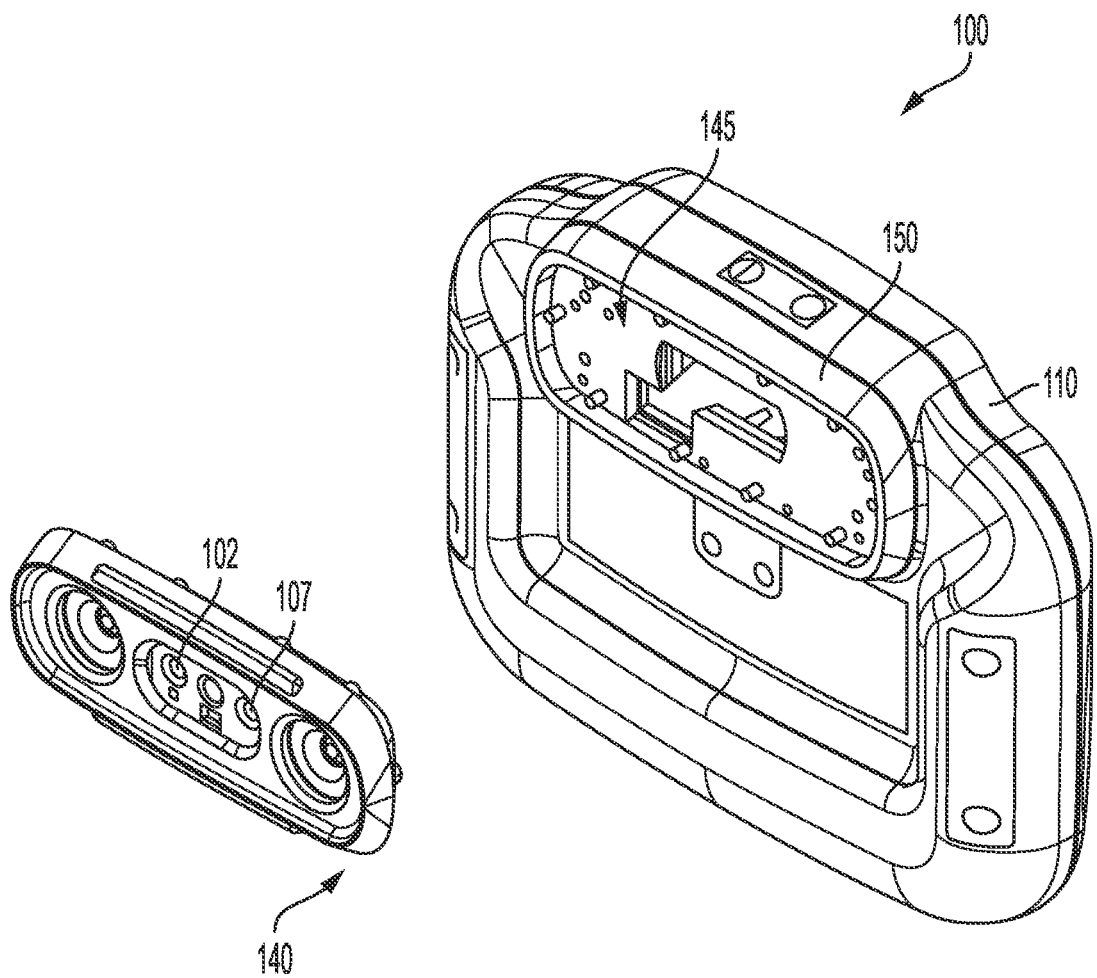
FIG. 5 is a perspective view of a first embodiment of an optical housing detached from a base housing of the handheld imaging system of FIG. 1.
Figure 6:
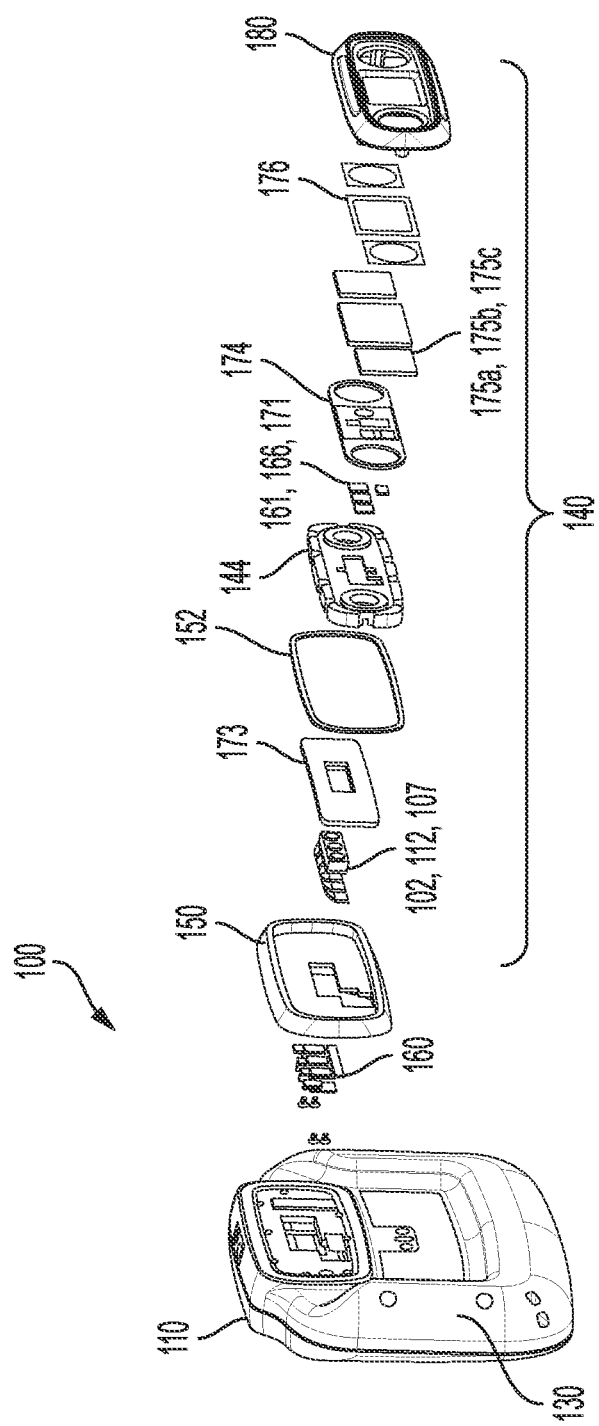
FIG. 6 is an exploded view of the optical housing of FIG. 5 detached from the base housing of the handheld imaging system of FIG. 1.
Figure 7:
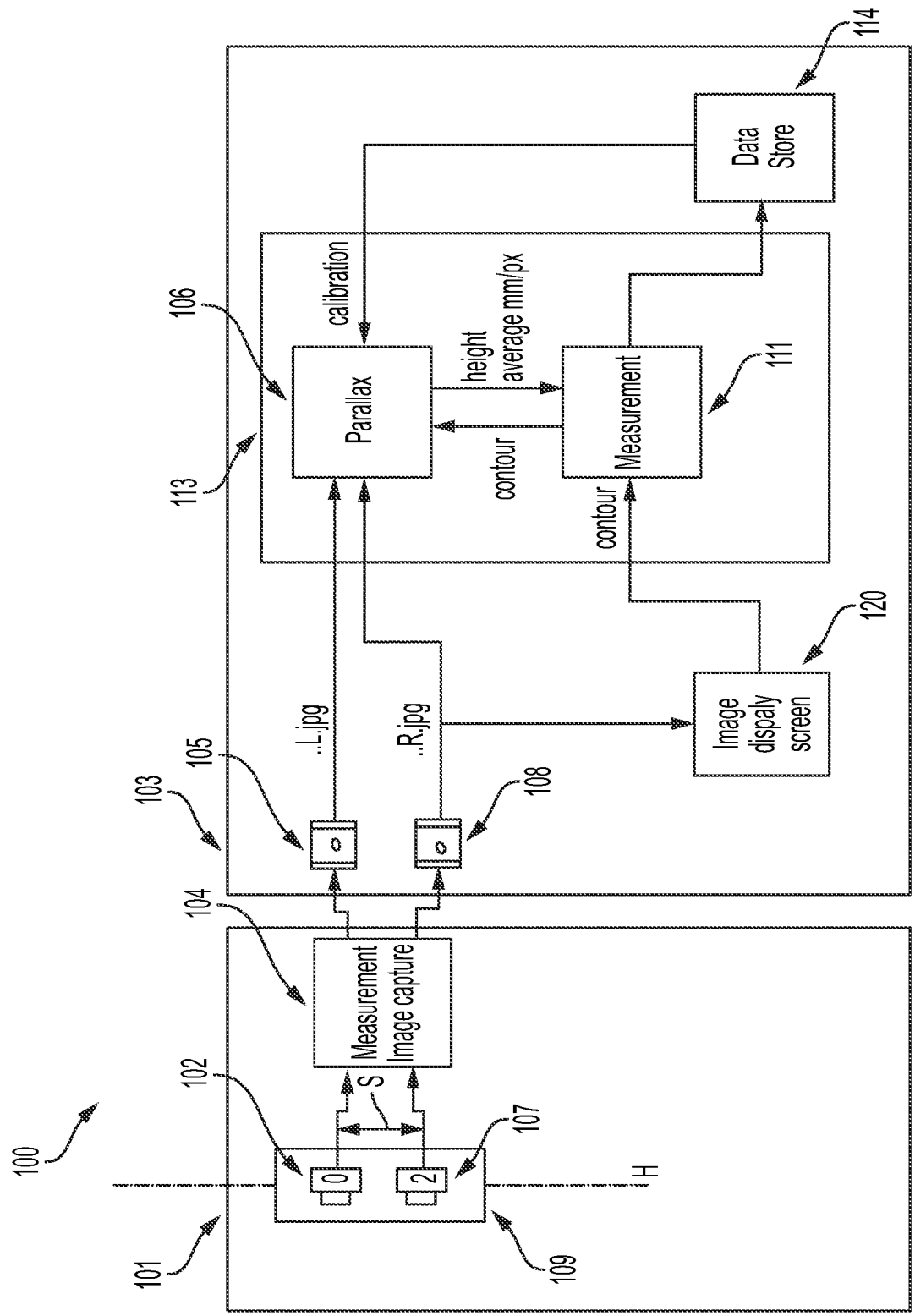
FIG. 7 is a block diagram illustrating exemplary image capture and analysis components used in the handheld imaging system of FIG. 1.

An exemplary embodiment of a portable, modular handheld imaging system 100 is shown in FIGS. 1-7. As illustrated schematically in the block diagram of FIG. 7, the imaging system 100 includes an imaging device 101 operably coupled to a computer 103. The imaging device 101 includes at least two camera sensors, such as, for example, a stereoscopic camera assembly 109 having a first, primary camera sensor 102 and a second, secondary camera senor 107. Although for ease of illustration the imaging system 101 of FIG. 7 depicts only two camera sensors, as described above, the present disclosure contemplates an imaging system 101 having any number of camera sensors (i.e., in addition to the camera sensors being utilized as the primary and secondary camera sensors 102 and 107), including, for example, camera sensors that may be used for one or more of WL, FL, IR, and thermal imaging. Furthermore, it will be understood by those of ordinary skill in the art, that the primary and secondary camera sensors 102 and 107 can have multiple functions in addition to providing images for contactless measurement, including, but not limited to, being used for WL, FL, IR, and/or thermal imaging. Furthermore, the camera sensors 102 and 107 can be utilized in an opposite manner, such that camera sensor 107 is used as the primary camera sensor and camera sensor 102 is used as the secondary camera sensor.

The camera sensors 102 and 107 are mounted in a horizontal plane H at a predetermined, fixed separation distance S. In other words, with reference to FIG. 2, the first and second camera sensors 102 and 107 are aligned along a plane H transverse to a longitudinal axis A of the imaging device 101 on opposite sides of the longitudinal axis A, wherein the longitudinal axis A passes through a top and a bottom of the imaging device 101. In accordance with various embodiments of the present disclosure the fixed separation distance S is at least about 1 mm. The separation distance S is determined, for example, by the typical distance between a camera and an object being imaged under a given imaging and measurement application. The objects being imaged must always be in the field of view of both cameras. Accordingly, those of ordinary skill in the art will understand how to modify the separation distance S based on a given distance between the cameras and object being imaged to always keep the object within the field of view of both cameras. The typical distance between the cameras and a wound under a wound imaging and measurement application is about 8 cm to about 20 cm.

The computer 103 includes, for example, a processor (i.e., CPU) 113, a memory, a program storage, an input/output, a display screen (i.e., image display) 120, and a data store 114. The display screen 120 may be a touchscreen to permit input from the clinician as a user interface. The processor 113 is programmed to perform the operations of the methods for contactless measurement as disclosed herein. For example, the processor is programmed to receive an output resulting from the operations of measurement image capture 104 (which may, in some implementations, be performed by a processor included in the imaging device 101), and to the perform operations of parallax calculation 106, and measurement calculation 111, as described in detail below.

Figure 8:
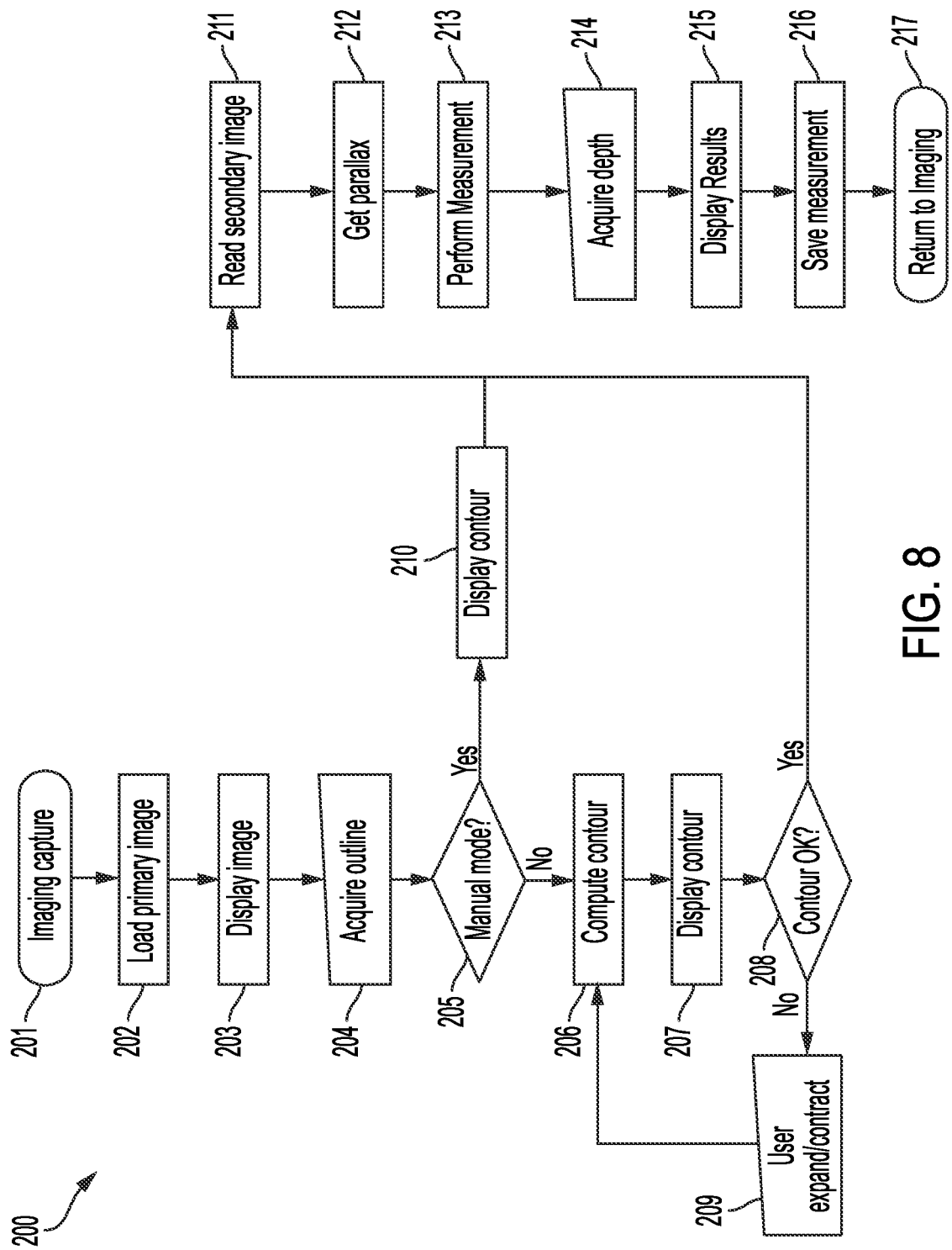
FIG. 8 is a workflow diagram illustrating an exemplary method for measurement according to the present disclosure.

With reference to the workflow diagram of FIG. 8, utilizing exemplary method 200, a person (e.g., a clinician) operating the system 100 may activate the processor 113 of the imaging device 101 to invoke the measurement image capture component 104, arrange the system 100 within a predetermined minimum and maximum range of distance from the object to be measured (i.e., the target) until the object appears in focus on the display screen 120, and then, when the target is in focus, depress a capture button (not shown) to actuate the image capture component 104 to perform image data capture step 201 to substantially simultaneously capture a primary image 105 with the first camera sensor 102 and a secondary image 208 with the second camera sensor 107. In steps 202 and 203, the computer 103 loads and displays the primary image 105 via display screen 120 to the clinician operating the device 101, thereby enabling the clinician to trace an outline (see outline 523 in FIG. 18) of the entire object of interest (OOI) or region of interest (ROI) within the imaged target on the display screen 120, in step 204. In this case the ROI is a wound on the surface of the skin. At this time, the clinician has two options to trace an outline of the wound displayed on the display screen 120. The clinician may optionally elect to manually outline the wound using a pointer of stylus in line drawing model (i.e., defining a contour region (see contour region 521 in FIG. 18) of the target within the captured primary image 105), in manual mode step 205. Alternatively, in step 206, the clinician may select to have the contour of the target automatically computed using any methods known to those of ordinary skill in the art, with the computed contour being displayed in step 207. The computed contour can also be optionally expanded or contracted in step 209 under the clinician's control, until the clinician is satisfied that the generated border line adequately follows the outline of the wound and accepts the contour in step 208..

After the contour is identified and accepted, the processor 113 may then activate the parallax computation 106, whereby the primary image 105 and the secondary image 108 are loaded, in step 211, together with predetermined camera calibration coefficients and the contour points to determine a parallax value for the target in step 212. In accordance with the present disclosure, the contour is placed on the same regions on both the primary and secondary image. The offset from the one image is thus identical to the other image. In accordance with an exemplary embodiment, the processor 113 may apply a parallax algorithm to shift the contour region of one of the primary and secondary images over the other. In accordance with one embodiment, the processor 113 may apply the parallax algorithm to shift the contour region of the secondary image 108 until it exactly overlaps the contour region of the primary image 105 to determine the parallax value for the target within the contour region, as discussed in more detail below. In another embodiment the processor 113 may apply the parallax algorithm to shift the contour region of the primary image 105 until it exactly overlaps the contour region of the secondary image 108 to determine the parallax value. It should be noted that the shift value and the parallax value are calculated as an absolute value. In this manner, the processor 113 may calculate a parallax pixel dimension for a geometric midpoint of the contour region expressed in millimeters-per-pixel (mm/pixel) for the primary image 105 using the determined parallax value.

Using the pixel dimension at the target, the processor 113 may calculate measurement data related to the target. Thus, after calculation of the pixel dimension at the target, the processor invokes a measurement computation component 111, by which the outputs of step 212 are used, in step 213, to compute measurement data related to the target, such as, for example, wound attributes, including, but not limited to, length, width and area using methods known to those of ordinary skill in the art. Optionally, the system 100 may also acquire a depth value of the wound, in step 214, for example, by requesting the clinician to manually enter the depth value.

Finally, in step 215, the processor 113 may output the measurement data to the display screen 120, such as, for example, by graphically and numerically displaying the wound attributes in visual combination with the primary wound image 105 and the wound contour.

Upon review and acceptance of the results by the clinician, the processor 113 saves the points of the contour region and resulting measurement data (i.e., wound attributes) to the persistent data storage 114 in step 216 and returns to the imaging device 101 in step 217.

Parallax Algorithm

Figure 9:
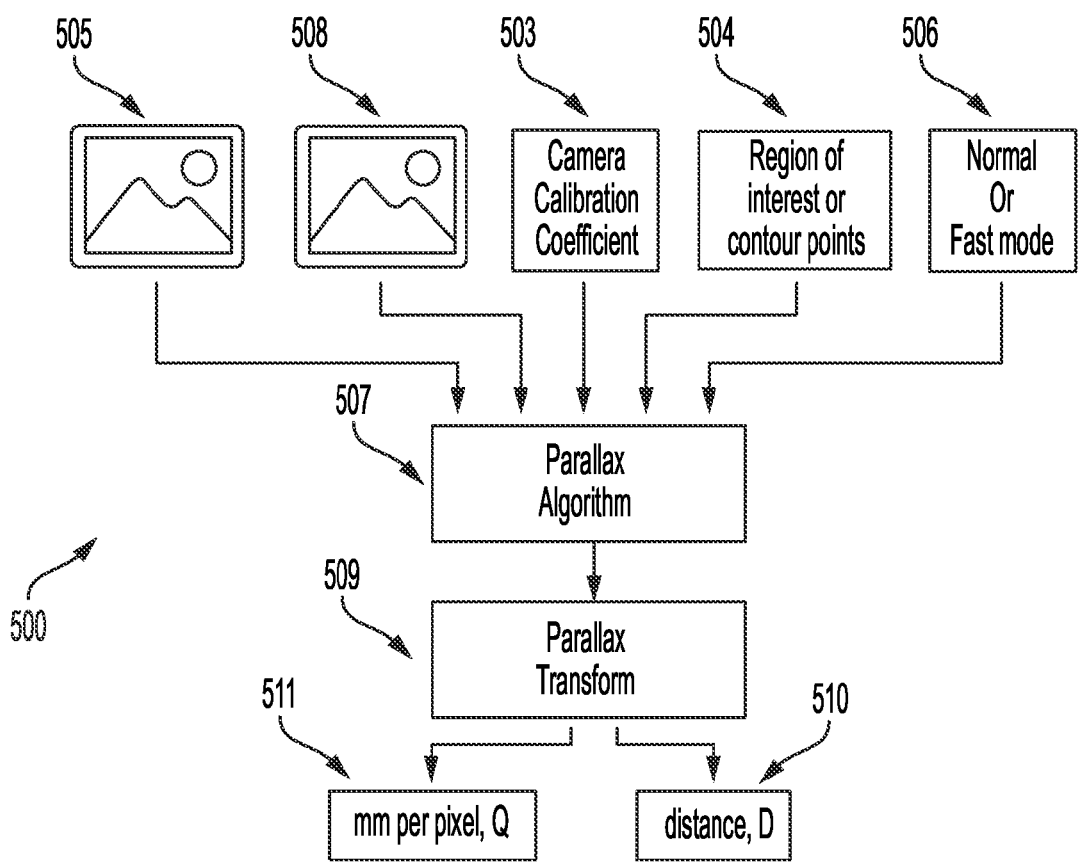
FIG. 9 is a block diagram illustrating exemplary parallax components as utilized by the imaging systems and methods of the present disclosure.

An exemplary parallax algorithm 507 as utilized within the handheld imaging system 100 and method for measurement 200 is now described with reference to FIG. 9. As illustrated in FIG. 9, the parallax algorithm 507 takes in two overlapping images of the same resolution, a primary image 505 and a secondary image 508, camera calibration coefficients 503, a region of interest 504 which may be a rectangular region or a more complex contour defined by a set of 2-dimensional points, and a mode 506 which controls the parallax algorithm 507 and outputs the pixel shift value as a number of pixels, which represents the shift between the two captured images.

In accordance with the present disclosure, the parallax algorithm 507 may calculate the pixel shift value by shifting the secondary image 508 until it exactly overlaps the primary image 505 (as noted above, the parallax algorithm 507 may also calculate the pixel shift value by shifting the primary image 505 until it exactly overlaps the secondary image 508). The algorithm 507 may determine when the images 505 and 508 are overlapped by performing a pixel-value subtraction at each pixel and capturing a new image of all the pixel subtractions. After shifting the images multiple times, the algorithm 507 determines when the secondary image 508 fully overlaps the primary image 505 by determining when an average brightness of all the pixels is at a minimum. In other words, the number of pixels shifted in order to produce the lowest average brightness of the pixels becomes the pixel shift value.

The parallax algorithm 507 subtracts the two images 505 and 508, one shifted and one not, pixel by pixel, and returns the average sum of the pixels. In accordance with various embodiments, the pixel subtraction is calculated by subtracting the red, green and blue (RGB) components. When an image is loaded into the parallax algorithm 507, for example, the image may be of two types: YUV_420 and RGB. To convert YUV to RGB, a transform function may be applied, as will be understood by those of ordinary skill in the art, and as further described below. Furthermore, since subtracting two pixels may result in a negative number, the algorithm 507 uses an absolute value of the difference. Therefore, the brightness of the new image is the absolute sum of the differences divided by the number of pixels.

Figure 18:
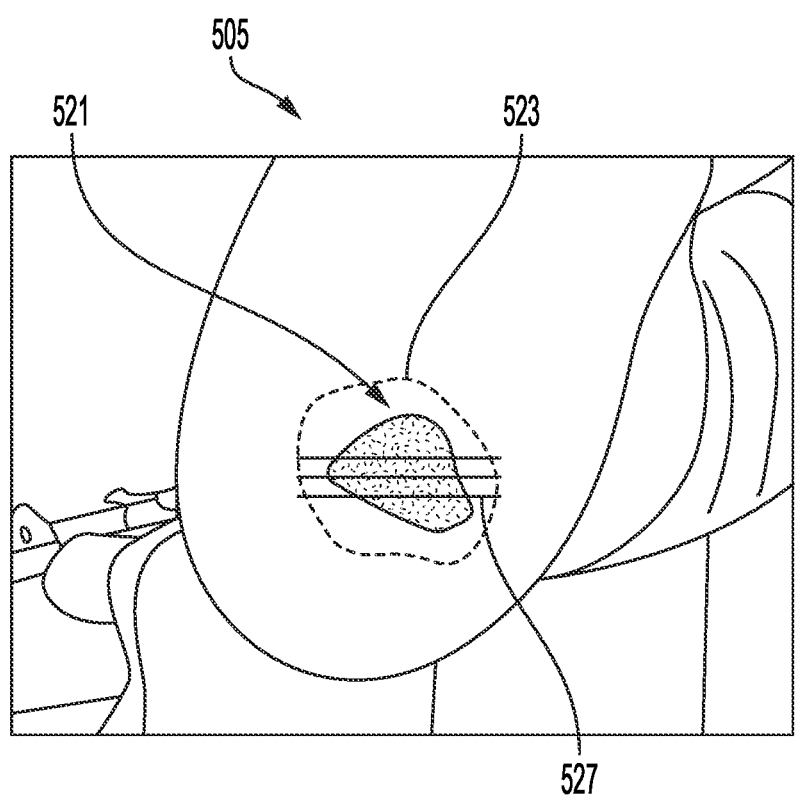
FIG. 18 illustrates an exemplary contour region drawn by a clinician.

As described above, theoretically each pixel is subtracted one-by-one; however, as there may be many pixels, resulting in increased processing time, for example, tens of seconds, the present disclosure contemplates various techniques to speed up computation and make implementation of the algorithm more practical and usable in real-time. For example, if a single row has 3264 pixels of 3 colors (RGB) and if each one is subtracted, this results in about 10,000 calculations per shift. And if there are 800 shift possibilities, this is almost 8 million calculations for the processor to run to calculate the pixel shift value. To reduce the load on the processor and speed up calculation of the pixel shift value, in one example embodiment, the parallax algorithm 507 may consider only a portion of the primary and secondary images 505 and 508, for example, the portions that are within the drawn border line enclosing the target's region of interest (i.e., a contour region), or contour points 504, more specifically a horizontal band of pixels, which are a preset number of pixels, for example 1 to 20, above and below the contour median. As illustrated in FIG. 18, for example, a clinician has drawn a border line 523 to enclose a contour region 523 in the primary image 505. In the illustrated embodiment, the parallax algorithm 507 will only consider three horizontal bands of pixels 527, wherein each band of pixels 527 is separated by about 50 pixels. Those of ordinary skill in the art will understand, however, that the primary image 505, border line 523, and bands of pixels 527 illustrated in FIG. 18 are exemplary only, and that parallax algorithms in accordance with the present disclosure may consider and utilize various portions of the contour regions to determine the parallax value and pixel shift value.

Those of ordinary skill in the art will also understand that the above discussed technique to reduce the computation time of the pixel shift value is exemplary only and that other techniques, modes and types may be created employing different values and combinations, without departing from the scope of the present disclosure. Furthermore, it will be understood by those of ordinary skill in the art that, when implementing the parallax algorithm 507, it may be advantageous in various embodiments to use a computer 103 that supports multiple processors 113, such that the processors may be instructed to execute as many of the image shift and subtraction operations as possible in parallel to optimize computing resources.

Parallax Transform

An exemplary parallax transform 509 as utilized by the parallax algorithm 507 is now described with reference to FIGS. 9 and 10. As described above, in one embodiment, the number of pixels shifted (the pixel shift value) may be passed to a parallax transform 509, wherein using the parallax transform method: (1) the number of pixels is converted to a target-plane mm/pixel value (Q) (see 511), and (2) a distance value (D) from the primary camera sensor 102 to the target is determined (see 510).

Figure 10:
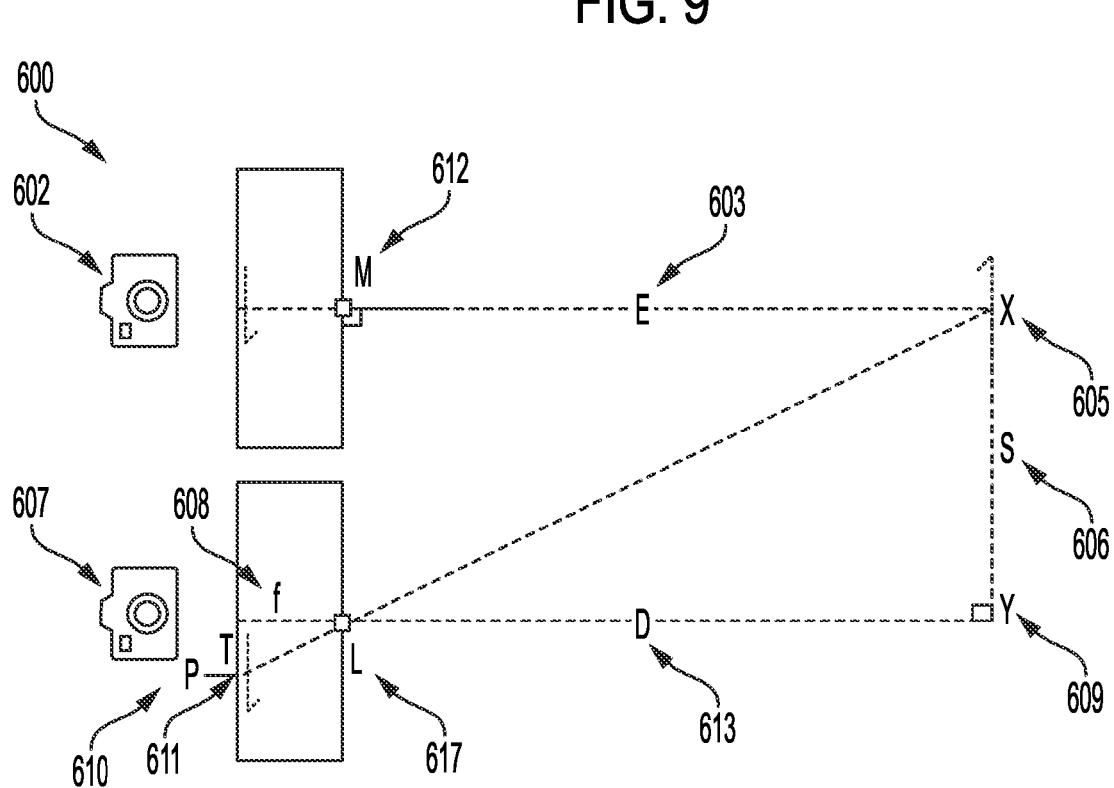
FIG. 10 is a diagram illustrating an exemplary parallax calculation geometry as utilized by the imaging systems and methods of the present disclosure.

With reference to FIG. 10, which illustrates an exemplary parallax calculation geometry 600, in accordance with the present disclosure, the parallax transform 509 can determine a distance D (613) to a target X (605), where:

M (612) is the primary camera sensor 602 lens, as a point in line with the target X's center, L (617) is the secondary camera sensor 607 lens, as a point separated by a fixed separation distance S (606), S (606) is the separation distance of the two cameras sensors 602 and 607, for example, in the exemplary embodiment of the system 100 of FIGS. 1-7, S is about 21 mm, but is determined by the field of view requirements, E (603) is a scalar distance of the target X to the lens M, f (608) is a focal length between the lens L and the sensor 607, which is a fixed value determined by the specifications for the camera. For example, in the embodiment of the system 100 of FIGS. 1-7, the focal length is about 3.05 mm, P (610) is the pixel shift value, corresponding to the number of pixels of the shifted secondary image from the secondary camera sensor 607 from the parallax algorithm (e.g., see element 506 in FIG. 9), T (611) is the parallax value in the image on the secondary camera sensor 607, for example, in millimeters, computed as the number of pixels P multiplied by the resolution R of the sensor 607, as fixed by the manufacturer, which in the embodiment of the system 100 is about 0.001413 mm/pixel, and D (613) is the distance to the target from Y (609), perpendicular to S, and parallel to E.

Using well-known trigonometry, the distance D to the target can be determined as:

$$D = f \frac{S}{T} \quad (1)$$

In the embodiment of system 100, for example, this may be:

$$D = 3.05 \frac{21}{0.001413 P} = \frac{45329}{P}$$

As also known in the art, the ratio of the focal length to the distance is equal to the ratio of the mm/pixel at the sensor (R) and at the target (Q):

$$Q = \left( f \frac{S}{P \cdot R} \right) \frac{R}{f} = \frac{S}{P} \quad (2)$$

In the embodiment of system 100, for example, this may be:

$$Q = \frac{21}{P}$$

The distance D and the pixel dimension Q of the target are expressed solely as a function of the number of pixels shifted (P). It is therefore important to measure P accurately. Due to the autofocus of most cameras, however, the focal length may vary, which may alter the value of (f) in the equations above. Furthermore, the separation distance S of the two camera sensors should be known within one pixel-width prior to calculating the parallax value, a tolerance that may be difficult to achieve due to manufacturing variations. To address these possible issues, exemplary embodiments of the present disclosure further contemplate calibrating the handheld imaging device to calculate a calibration coefficient for each imaging device, the calibration coefficient to be saved and used in calculating the parallax.

Camera Calibration

As described above, a target's pixel dimension Q (i.e., mm/pixel) is expressed as a function of the number of pixels shifted. This is true for a linear system. However, due to external factors, including auto-focus, image field-of-view misalignment, and tolerances in the mechanical mounting of the camera sensors, the parallax transform 509 has non-linearities that may introduce errors. In accordance with various embodiments, these non-linearities may be measured during a calibration procedure to generate calibration coefficients suitable for use in a linear regression algorithm, as described further below, which may then be applied to the parallax transform 509 during the measurement operation to compensate for the errors.

In one exemplary embodiment, the system and methods of the present disclosure may further utilize a method for compensation of non-linearities, including:

capturing calibration images using a calibration apparatus, calculating manufacturing coefficients from the captured calibration images, calculating non-linear point coefficients from the captured calibration images, recording these as calibration coefficients to a persistent calibration file, loading the persistent calibration file for use by the parallax algorithm during parallax calculation, applying the manufacturing coefficients to offset the secondary image to compensate for manufacturing offsets, determining the parallax value from the primary image and offset secondary image, and running a linear regression algorithm on the parallax value using the non-linear point coefficients to compute the distance (D) and the pixel dimension (Q).

Figure 11:
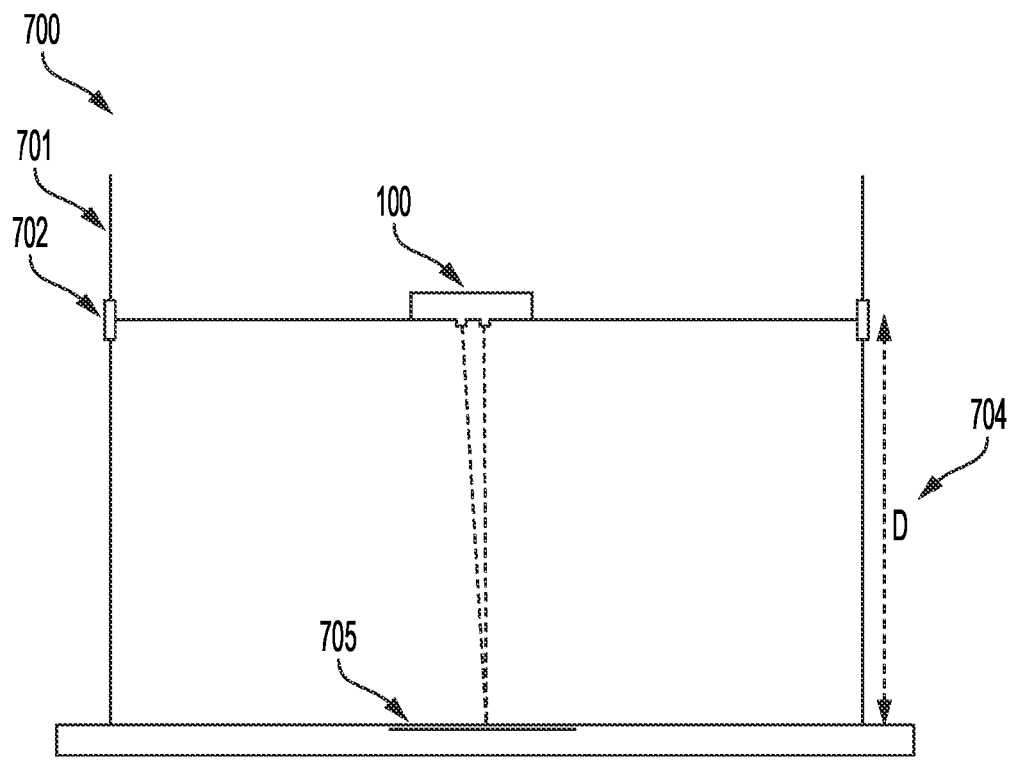
FIG. 11 illustrates an exemplary calibration apparatus as utilized by the imaging systems and methods of the present disclosure.

With reference to FIG. 11, an exemplary calibration apparatus 700, for use with the above calibration method to calibrate, for example, the imaging system 100, is shown. In accordance with one embodiment, the calibration apparatus 700 includes a vertical frame 701 and a camera mount 702, on which the imaging system 100 may be mounted, such that the camera mount 702 is vertically adjustable and able to position the stereoscopic cameras (e.g., the camera sensors 102 and 107) to predetermined vertical positions D relative to a calibration object target 705 within a given accuracy, such as, for example, to an accuracy of about 1 mm.

Figure 12:
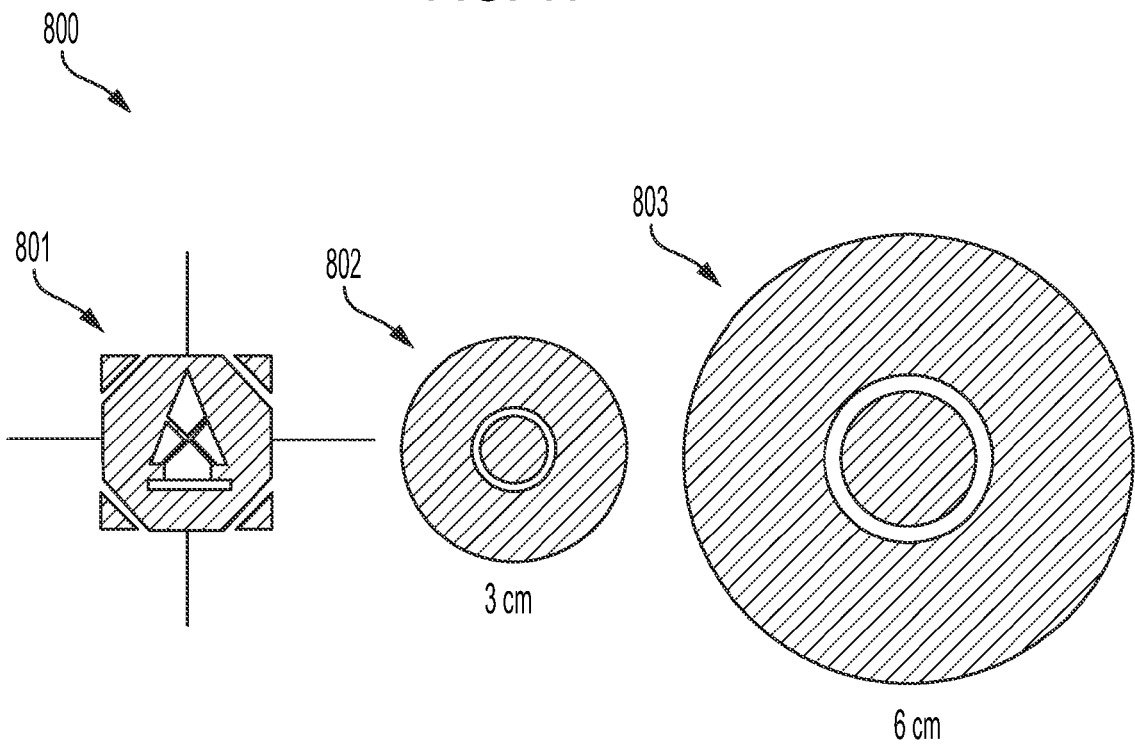
FIG. 12 illustrates exemplary calibration object targets as utilized by the imaging systems and methods of the present disclosure.

With further reference to FIG. 12, the calibration object target 705 may be a set of predefined object targets 800, such as printed paper targets, each of a specific geometry and size. In an exemplary embodiment, with the camera mount set to a predetermined known vertical position, for example of about 12 cm, a target with a printed image 801 is captured using the camera sensors to obtain a primary and a secondary image. The primary image may be used as the reference image and the secondary image may be shifted horizontally, using the parallax algorithm (e.g., 507) as taught herein, until the pixel shift value, in pixels, is found.

With the camera mount set to a different predetermined vertical position, for example, 8 cm, 12 cm, 16 cm, or 20 cm, a target with an appropriately sized printed image, which fills for example approximately half the field of view, is captured using the stereoscopic cameras sensors to obtain a primary and a secondary image (e.g., 105, 505 and 108, 508). For larger vertical positions, such as for example, vertical positions of about 16 cm and greater, a larger image 803 (e.g., a 6 cm image) may be used. And for closer vertical positions, such as for example, vertical positions under about 16 cm, a smaller image 802 (e.g., a 3 cm image) may be used. The manufacturing coefficients of vertical shift and rotation may then be applied to the secondary image in the parallax algorithm, as taught herein, to determine the pixel shift value in pixels for each set of images.

In accordance with various embodiments, for example, at different vertical positions, the following data may be recorded and stored as non-linear coefficients for each vertical position point: (1) the vertical position distance of the camera to the image, (2) the pixel shift value at that distance, (3) the measured width of the object in pixels, and (4) the known width of the object in millimeters (mm). In calibrating the imaging system 100, this step may be repeated for a number of different vertical positions, for example 3 or 4 different vertical positions, to get a sufficient number of calibration points to use to accurately calculate the parallax value. Once the calibration coefficients have been obtained through this calibration process, they may be stored, for example, in a persistent calibration file, an example of which is shown below:

```
{
    "Version": "1.0",
    "Name": "Optical Only",
    "Shift": 488,
    "Cam_0": 0,
    "Cam_1": 1,
    "Alignment": -18,
    "Rotation": 0.6875,
    "Fov_Ratio": 0.9853124999999999,
    "Fov_Offset_X": -200,
    "Fov_Offset_Y": 367,
    "LightType": 0,
    "Calc_Min": -400,
    "Calc_Max": 1100,
    "Calc_Step": 16,
    "CAL_Total": 3,
    "CAL_000": "179;937;200;60",
    "CAL_001": "270;1178;160;60",
    "CAL_002": "727;1205;80;30"
}
```

In accordance with various exemplary embodiments, this file may include a vertical shift, secondary image scale factor, and rotation for the secondary image (e.g., 108, 508), and a list of values for each calibration point.

Linear Regression Transforms

As discussed above, the present disclosure contemplates calculating a target-plane mm per pixel dimension (Q) and a distance to the target (D) in the presence of non-linearities by a least-squares linear regression algorithm that is well known in the art. In accordance with various embodiments, for example, the least-squares linear regression algorithm may be applied as follows:

to avoid negative parallax values, a fixed offset value is chosen to add to the parallax to ensure the parallax is positive for all valid ranges of use;

from the list of coefficient points, parameters α and b are derived by standard linear regression algorithms to linearize the non-linear point coefficients;

α and b are used in the transformation of the values of target-plane parallax to pixel ratios (Q), whereby:

$$Q = \alpha(x+o) + b \quad (3)$$

wherein x is the parallax value and o is the fixed offset value as taught herein;

from the list of coefficient points, parameters α and b are also used in the transformation of the values of parallax to distances (D), whereby:

$$D = \frac{1}{\alpha\sqrt{(x+o)} + b}^2 \quad (4)$$

wherein x is the parallax value and o is the fixed offset value. In this manner, the distance (D) will change by the inverse square of the parallax value x.

As will be understood by those of ordinary skill in the art, the use of more calibration points may result in more accurate values for Q and D. Additionally, since the linear regression algorithm interpolates between calibration points and extrapolates when used outside of the range of points, the operation range of the imaging system (e.g., system 100) is not limited by the calibration points used. For example, if the calibration includes coefficients for 8 cm and 16 cm distances, the parallax algorithm can still determine the mm/pixel (Q) at 12 cm (i.e., by interpolating) and 20 cm (i.e., by extrapolating) by way of linear regression. Furthermore, the non-linearities previously mentioned, including, for example, manufacturing tolerances, focal depth non-linearities, and offsets between the two camera sensor views may be accommodated by the camera calibration method, as discussed above.

Real-Time Range-Finding and Focusing

In various additional embodiments of the present disclosure, the parallax transform, such as, for example, transform 509 as discussed above with reference to FIG. 9, may be used to determine the distance from the camera to the target in real time from stereoscopic camera sensor image previews prior to image capture. In accordance with various embodiments, coarse and medium iterations of the parallax algorithm 507 and other improvements, as taught herein, may be employed to provide acceptable accuracy in real time, for example, within about a 10% accuracy, for the distance measurement. In one embodiment, for example, the imaging system 100 may be prevented from taking images (i.e., image capture may be prevented) if the distance to the target is unknown or not within an acceptable range.

To get stable and consistent values from the parallax algorithm 507, both stereoscopic camera sensors 102 and 107 also must be focused. Accordingly, in another embodiment, the parallax algorithm 507 may be used in real time, as taught herein, to detect when the parallax values are stable, thereby indicating that the camera sensors 102 and 107 are in-focus. And, if the camera sensors 102 and 107 are not in-focus, the imaging system 100 may be prevented from taking images (i.e., image capture may be prevented).

Synchronizing Stereoscopic Cameras

Furthermore, to determine a parallax value accurately, the stereoscopic images must be synchronized to ensure that the cameras do not move between the time that the first image is captured and the time that the second image is captured. For the purposes of a handheld imaging system, such as, for example, the imaging system 100 described herein, precise hardware synchronization is not necessary. In various embodiments, for example, the processor 113 can trigger capture of both the stereoscopic images 105, 505 and 108, 508 when: a capture button is pressed, all previous capture operations have completed, both camera views are stable (i.e., not changing much), both camera sensors 102 and 107 have completed their focus operations, and the distance from the target to the camera sensors 102 and 107 is within the predefined range. Thereafter, the stereoscopic images 105, 505 and 108, 508 are locked in a temporary memory storage, while the time-consuming operations, including, for example: applying overlays, adding metadata, resizing, compressing, and moving to the data storage 114 are performed.

Multiple Regions of Parallax

The parallax algorithm (e.g., the parallax algorithm 507), functions best when the target is flat, in a substantially horizontal plane, and the imaging system 100 is positioned directly above the horizontal plane such that the line from one stereoscopic camera sensor to the other camera sensor is parallel to the horizontal plane. Since when applying the algorithm 507 such optimal conditions are often not possible, embodiments of the present disclosure further contemplate employing various alternatives.

Figure 13:
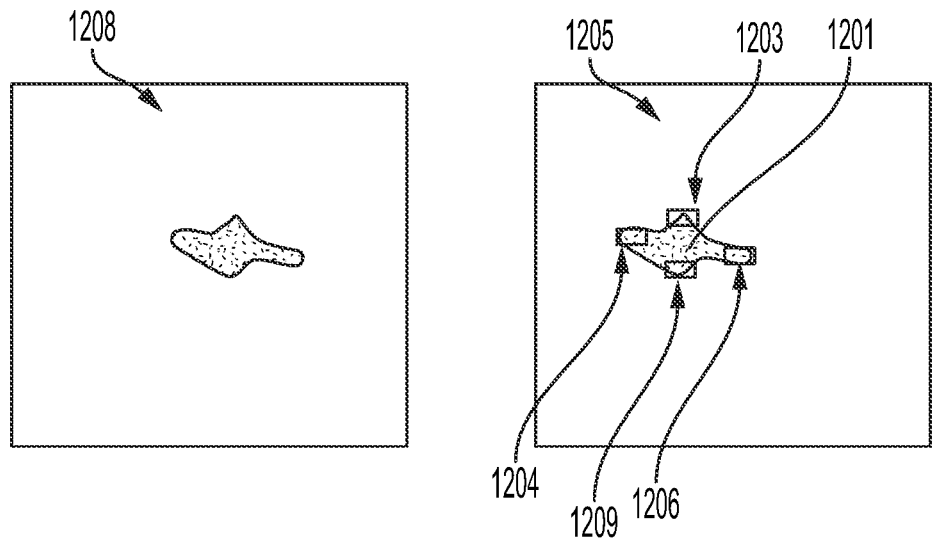
FIG. 13 illustrates application of a parallax algorithm to images of angled objects.

In one exemplary embodiment, the systems and methods of the present disclosure contemplate measuring multiple parallax regions to determine an angle between the imaging system 100 and a plane of the target. For example, as illustrated in FIG. 13, which illustrates a primary image 1205 and a secondary image 1208, a contour region 1201 of the target in the primary image 1205 may be used to determine parallax regions, such as, for example, rectangles at the left 1204, right 1206, top 1203 and bottom 1209 extremities of the contour region 1201. By comparing the distance values at each of these smaller regions 1204, 1206, 1203, and 1209, the angle of the target's plane to the camera sensors 102 and 107 may be calculated. Simple trigonometry may then be used to correct the computed dimensions and area of the target to compensate for the angle of the target's plane, as will be understood by those of ordinary skill in the art.

Figure 14:
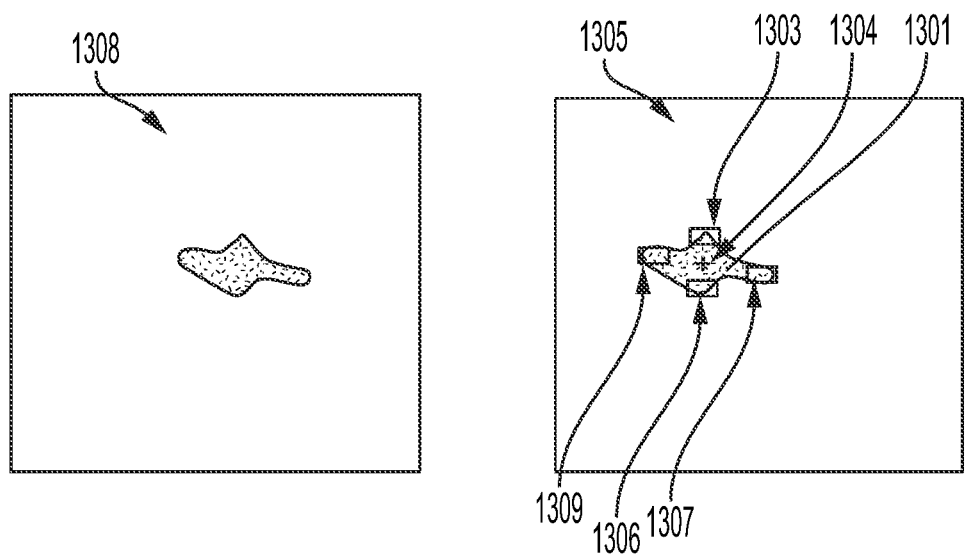
FIG. 14 illustrates application of a parallax algorithm to images of curved objects.

In yet another exemplary embodiment, the systems and methods of the present disclosure contemplate measuring multiple parallax regions to determine a curvature of the target's surface, which may be either concave or convex. For example, as illustrated in FIG. 14, which illustrates a primary image 1305 and a secondary image 1308, in addition to a parallax at a center 1304 of the target, a contour region 1301 of the target in the primary image 1305 may be used to determine parallax regions, such as rectangles at the left 1309, right 1307, top 1303 and bottom 1306 extremities of the contour region 1301. By mapping the distance values at the center 1304 and each of these smaller regions 1309, 1307, 1303, and 1306, the curvature of the target's plane to the camera sensors 102 and 107 may be calculated. Simple geometry may then be used to correct the computed dimensions and area of the target to account for the curvature of the target, as will be understood by those of ordinary skill in the art.

Managing Reflections of Light and Eliminating Bright Reflections

Figure 15:
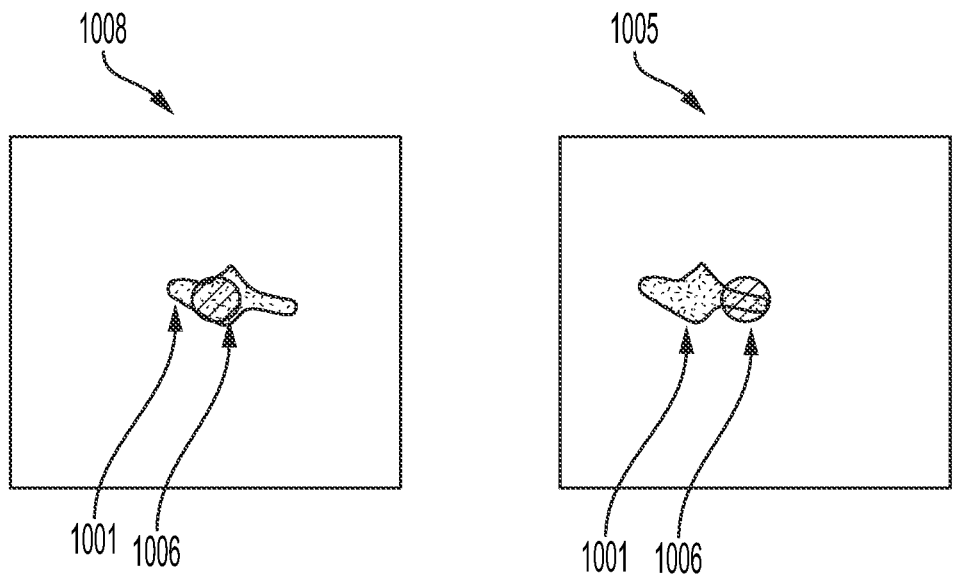
FIG. 15 illustrates images with white light reflection.

The parallax algorithm (e.g., the parallax algorithm 507) may also be confused by light that is reflected from the target. For example, if the target has a shiny surface, the target may reflect light from a concentrated light source (e.g., from a built-in white-light source that is used to illuminate the target) to each of the stereoscopic camera sensors 102 and 107 in a way that creates a glare on the images 105 and 108 and confuses the parallax algorithm 507. With reference to FIG. 15, which illustrates a primary image 1005 and a secondary image 1008, the illustration shows how a reflection 1006 on a target 1001 in the primary image 1005 can appear at a different location on the target 1001 in the secondary image 1008. In various embodiments, the systems and methods of the present disclosure may be configured to pre-process the camera images 1005 and 1008 to blacken out pixel clusters with extremely bright reflections of light, thereby ensuring that the reflections are not used in the parallax algorithm 507.

In various additional embodiments, the systems and methods of the present disclosure may exclude parallax values resulting from reflections, by performing multiple applications of the parallax algorithm 507 at slightly differing y-locations from the contour median and accepting the results only of the parallax values that are within a small deviation of each other. The algorithm 507 may then average the accepted results to provide a final result.

Patterned Objects

Figure 16:
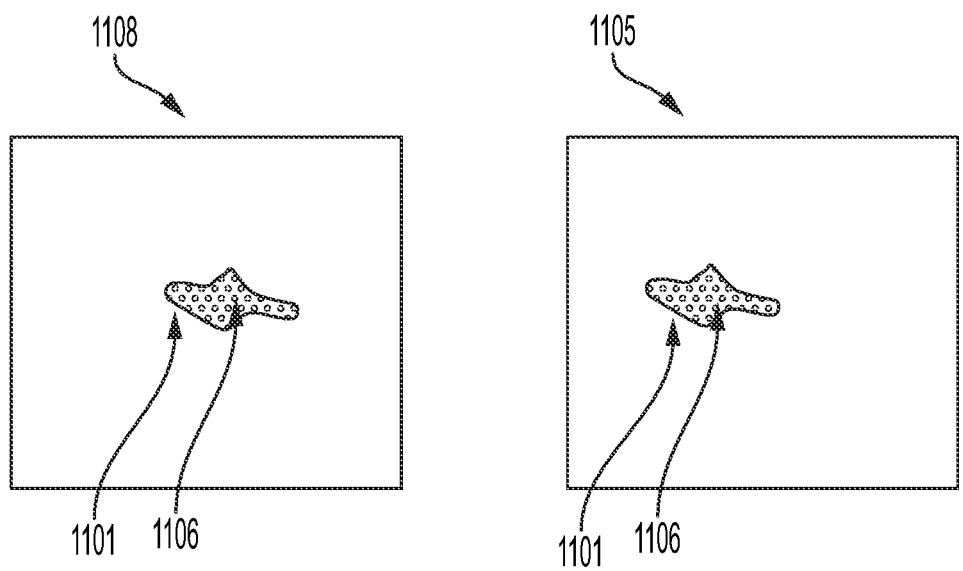
FIG. 16 illustrates images with repetitive patterns.

The parallax algorithm (e.g., the parallax algorithm 507) may further be confused by targets having repetitive patterns. For example, repetitive patterns displayed in the camera sensor images 105 and 108 may confuse the parallax algorithm 507 by causing false minima to be detected in the parallax algorithm 507. With reference to FIG. 16, which illustrates a primary image 1105 and a secondary image 1108, a target 1101 in the primary image 1105 may show a pattern 1106 that leads to a false minima in the object 1101 in the secondary image 1108. In various embodiments, the disclosed systems and methods may be further configured such that the parallax algorithm 507 may also reduce the detection of false minima by widening the contour region to include the border of the target and performing multiple applications of the parallax algorithm 507 at slightly differing y-locations from the contour median. The algorithm 507 may then only accept the results of the parallax values that are within a small deviation of each other and average the accepted results to provide a final result.

Topology of the Target

In a further embodiment, the systems and methods of the present disclosure may also determine a topology of the target by performing an additional computational analysis, including, for example:
- capturing each difference (i.e., Δ between primary and secondary images) that is generated, as the images are shifted multiple times and subtracted as taught herein;
- recording a pixel shift value for each captured difference;
- identifying points in the images of the captured differences in which the difference is smallest, and associating the corresponding pixel shift values with those points;
- assigning the pixel shift values of the associated points to corresponding locations $P_{xy}$ on the primary image;
- averaging the pixel shift values where there are multiple shift values assigned to the same locations $P_{xy}$;
- determining a distance D from a primary camera sensor to a geometric center of the target;
- determining a distance $D''$ from the primary camera sensor to each location $P_{xy}$ according to its pixel shift value as taught herein;
- subtracting $D''$ from D to obtain a surface height $H''$ perpendicular to a camera plane at location $P_{xy}$ relative to the geometric center of the target; and
- saving a map of height values $H''_{xy}$ to form a topological image of the target.

Those of ordinary skill in the art will understand that the computational analysis outlined above is exemplary only and that additional steps and/or processes may be utilized to compute various characteristics of the target, including, but not limited to the target's topography, using the pixel shift and/or parallax values as disclosed herein. Other embodiments of the disclosure will be apparent to those skilled in the art from consideration of the specification and practice of the teachings disclosed herein. For example, in accordance with various embodiments as discussed above, the present disclosure contemplates utilizing the disclosed systems and methods for contactless measurement (i.e., utilizing the parallax algorithm 507 and transform 509) in clinical applications, for example, in combination with wound assessment and analysis systems and techniques.

Example Imaging Systems

In one example embodiment, as disclosed, for example, in International Patent Publication WO 2020/148726, filed internationally on Jan. 17, 2020, which claims benefit to U.S. Provisional Application No. 62/793,842, filed Jan. 17, 2019, the entire content of each of which is incorporated by reference herein, the disclosed imaging system is a portable, handheld wound imaging system, which utilizes various combinations of white light (WL) imaging, fluorescence (FL) imaging, infrared (IR) imaging, thermal imaging, and/or three-dimensional mapping, and may provide real-time wound imaging, assessment, recording/documenting, monitoring and/or care management. The system may be hand-held, compact and/or lightweight.

In accordance with this example embodiment, the system may include first and second white light camera sensors configured to provide stereoscopic imaging and to capture primary and secondary images in practice of the methods described above. In addition, the system may further include at least one excitation light source configured to emit excitation light during fluorescent imaging; an excitation filter configured to detect and permit passage of optical signals, responsive to illumination of the target with the excitation light and having a wavelength corresponding to one or more of bacterial fluorescence, bacterial autofluorescence, tissue fluorescence, and tissue autofluorescence, to a third camera sensor configured to detect the optical signals responsive to illumination of the target with the excitation light. Other components of the imaging device may include a white light source configured to emit white light during white light imaging; a white light filter configured to permit passage of optical signals, responsive to illumination of the target with the white light and having a wavelength in the visible light range, to one of the first and second camera sensors of the imaging device. In this embodiment, the processor is configured to perform the methods described above with regard to calculation of the parallax value and pixel ratio to obtain measurements of the imaged target. The processor is further configured to receive the detected fluorescent and white light optical signals and to output a representation of the target to the display based on the detected optical signals. This example embodiment of the system and method may be suitable for the monitoring of wounds in humans and in animals.

In another example embodiment, the imaging system may be a portable, modular handheld imaging system. In such an embodiment, the imaging system comprises a base body portion, also referred to herein as a base portion or a base housing, which houses the processor, and an optical portion also referred to herein as an optical head, an optical housing or an optical housing portion, which houses the optics of the imaging device, including illumination and/or excitation light sources, camera sensors, and filters. The optical portion is releasably received by the base body portion and is interchangeable with other optical portions, each optical portion being configured for a particular application or to capture particular characteristics of and optical information from the target being imaged. Thus, a user will select an optical housing based upon the capabilities desired for imaging in a given situation.

The modular handheld imaging system may be packaged and/or sold as a part of a kit, where the base body portion and two or more optical housing portions are provided, the optical properties of each optical housing portion differing from each other and any other optical housing portions. The properties that may vary from one optical housing portion to another include the following non-limiting examples, which may be included in any combination in each optical housing portion: number of camera sensors (i.e., number of camera sensor in addition to the primary and secondary camera sensors), number of camera sensors configured for white light imaging (i.e., combined with filter for white light imaging); number of camera sensors configured for fluorescent imaging, wherein different camera sensors for fluorescent imaging may be paired with different filters to permit passage of different ranges of fluorescent emissions, wherein each range is configured to capture a particular characteristic of a target (e.g., vasculature or microvasculature, collagen, elastin, blood, bone, bacteria, malignancy, lymphatics, immune cells, adipose tissues, cartilage, tendons, nerves, gastrointestinal tissues, skin, pre-malignant or benign tissues, bodily fluids, urine, blood, saliva, tears, mucus, mucosal tissues, dermal tissues, and exogenous fluorescent agents, drugs, etc.). Furthermore, it will be understood by those or ordinary skill in the art that the camera sensors are configured to capture still images and/or video.

The number and type of excitation light sources may vary between optical housing portions as well. The excitation light sources are configured to emit excitation light having a wavelength of about 350 nm – about 400 nm, about 400 nm – about 450 nm, about 450 nm – about 500 nm, about 500 nm – about 550 nm, about 550 nm – about 600 nm, about 600 nm – about 650 nm, about 650 nm – about 700 nm, about 700 nm – about 750 nm, about 750 nm – about 800 nm, about 800 nm – about 850 nm, about 850 nm – about 900 nm, about 900 nm – about 950 nm, about 950 nm – about 1000 nm, and/or combinations thereof. In accordance with various embodiments, for example, the at least one excitation light source is configured to emit excitation light having a wavelength of about 405 nm ± 10 nm. In one exemplary embodiment, the at least one excitation light source includes first and second violet/blue LEDs, each LED configured to emit light having a wavelength of 405 nm ± 10 nm.

The shape of the optical housing portion may also vary from one housing to another, depending upon the particular application. For example, specialized shapes may be used for particular applications such as, for example, accessing confined anatomical spaces such as recesses, oral cavities, nasal cavities, anal area, abdominal area, ears, etc. In such cases, the optical housing may have the form of an endoscopic attachment. The materials forming the optical housing may vary from one housing to another. For example, the housing may have a flexible patient-facing portion or a rigid patient facing portion, dependent upon the application in which the imaging device is to be used. The optical housing may be made waterproof or water resistant in some embodiments. The housing may, in some embodiments, be made of materials that are inherently resistant to bacterial growth or be made of a material with a surface texture or topology that is resistant to microbial growth, e.g., roughened nanosurface. The size of the optical housing may vary depending upon the size and number of components contained therein. Various exemplary embodiments of the optical housing portions may also include, in any combination, features such as an ambient light sensor, a range finder, thermal imaging sensors, structured light emitters, an infrared radiation source and detector to be used for three-dimensional imaging, lasers for taking measurements, etc. Additionally or alternatively, the imaging system may also and have an external channel embedded in the housing to enable delivery of a tool such as a biopsy forcep, optical fiber spectroscopy probe or other implement that requires (FL) image guided targeting to collect tissue, ablate tissue, cauterize tissue or interrogate tissue that is fluorescent.

The base body portion/base housing includes an interface configured to releasably receive the optical housing portion. The optical housing portion includes a part configured to be received into the base body portion in a manner that provides electrical and power connections between the components in the optical housing portion and the battery and processor in the base body portion. The connection will enable data transfer between the optical housing and the base, which contains the processor configured to receive data from the imaging device (e.g., the camera sensors). Additionally, the base can be connected to a PC to store or analyze the data form the modular imaging device.

In various example embodiments, the base body portion further includes a heat sink. In one example embodiment, the heat sink forms a lip around the opening in the base body portion that is configured to receive the optical housing portion.

As discussed above, in one exemplary embodiment, the imaging system 100 is a portable, modular handheld imaging system for imaging and analysis of wounds in tissue, as illustrated, for example, in FIGS. 1-7. In such an embodiment, the imaging system 100 comprises a base body portion 110, also referred to herein as a base portion or a base housing, which houses the processor 113, and an optical portion 140 also referred to herein as an optical housing or optical housing portion, which houses the imaging device 101. As shown in FIGS. 1-7, in some example embodiments, the base body portion 110 of system 100 may have a generally square or rectangular shape. A front, or user-facing side 115 of the base body portion 110 includes a display screen 120 for displaying images and videos captured by the system 100. Although depicted as square or rectangular, the system 100 may take on any shape that will reasonably support a display screen such as a touchscreen display. In addition to disclosing images captured by the imaging system 100, the display screen 120 also operates as a user interface, allowing the user to control functions of the system via touchscreen input.

Figure 4:
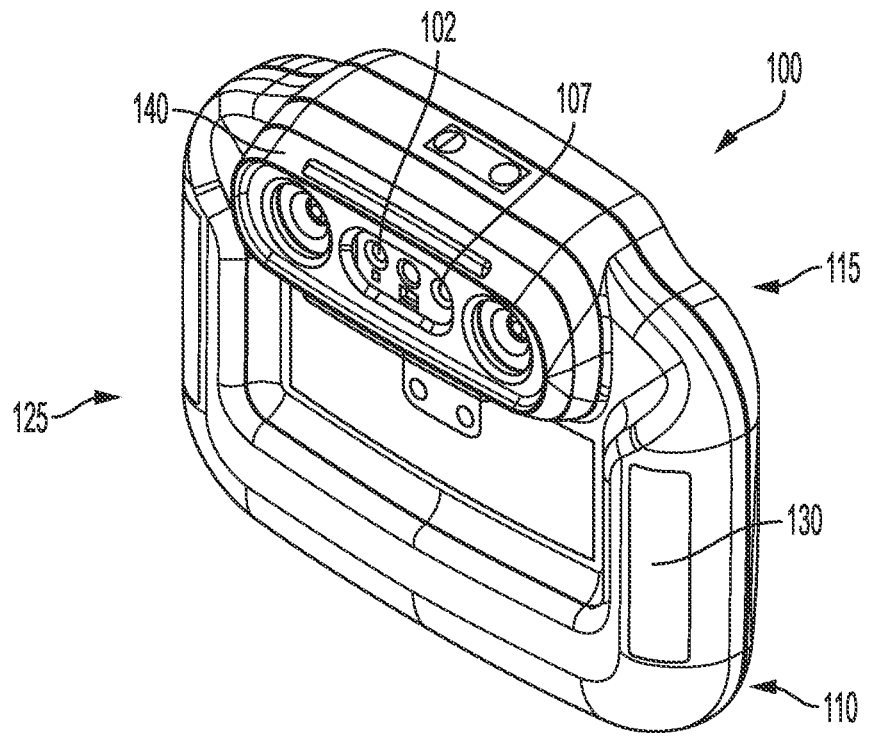
FIG. 4 is a rear perspective view of the handheld imaging system of FIG. 1.

Positioned on an opposite side of the system 100, on the patient-facing side 125 of the system, may be handhold areas 130 configured to facilitate a user holding the system during imaging. As illustrated in FIG. 4, the handhold areas 130 may comprise protrusions or areas that extend away from the base body portion 110 sufficiently to allow a user's fingers to grip or wrap around the protrusions. Various other types of handholds as well as alternative positioning of the handholds may be used. One consideration in the position of such handholds is the ability of the user to balance the imaging system 100 using the system for imaging and while inputting commands via the touchscreen display 120. Weight distribution of the imaging system 100 will also be a consideration to provide a user-friendly and ergonomic device. The patient-facing side 125 of the system 100 may also incorporate contacts 135 for wireless charging of the system.

In accordance with one aspect of the present disclosure, the patient-facing side 125 of the system 100 also includes an optical housing 140. The optical housing portion 140 may be detachable from the base body portion 110 as illustrated in FIG. 5. The optical housing portion 140 is illustrated as a rectangular housing configured to be received in a rectangular opening 145 on the base body portion 110. However, both optical housing portion 140 and opening 145 may take other shapes, such as for example square, oblong, oval or circular. Further, optical housing portion 140 may not have the same shape as opening 145 but instead a connector element having the same shape as or otherwise configured to be received in opening 145 of base body portion 110 may be used as a bridge to connect optical housing portion 140 to base body portion 110. The opening 145 is configured to releasably receive the optical housing portion 140. When the optical housing portion 140 is positioned in opening 145, it may be locked into position such that optical housing portion 140 is locked to base body portion 110. In this configuration, electrical contacts are made between base body portion 110 and the optical components contained in optical housing portion 140 and the components in the optical housing portion are powered by a power source, such as a battery, contained in the base body portion 110.

In various example embodiments, the base body portion 110 includes a heat sink 150. In one example embodiment, the heat sink 150 forms a lip around the opening 145 in the base body portion 110 that is configured to receive the optical housing portion 140.

In accordance with various embodiments of the present disclosure, the optical housing 140 may take on different shapes or configurations. In one embodiment, as shown in FIG. 5, the optical housing portion 140 has a generally flat, oblong shape. The optical components, including the primary camera sensor 102 and the secondary camera sensor 107, are arranged in a generally linear manner across a width of the optical housing 140, as discussed above with reference to FIG. 2. In another embodiment, not shown, the optical housing may, for example, include an endoscope portion. Unlike optical housing portion 140, in such an embodiment, the optical components contained in the optical housing, including the primary camera sensor 102 and the secondary camera sensor 107, are contained in a distal tip of the endoscope portion of the optical housing. As will be understood by those of ordinary skill in the art, the arrangement of the optical components may vary in each optical housing based upon the size and shape of the optical housing, as well as the number and type of optical components contained in a given housing, while maintaining the required arrangement and separation distance (i.e., between the primary camera sensor 102 and the secondary camera sensor 107) for the parallax calculation as discussed above.

In addition to the primary and secondary camera sensors 102 and 107, the optical housing portion 140 can include various optical components configured to facilitate the collection of optical signals from a target being imaged. The properties that may vary from one optical housing to another include the following non-limiting examples, which may be included in any combination in each optical housing: total number of camera image sensors, number of image sensors configured for white light imaging (i.e., combined with filter for white light imaging); number of image sensors configured for fluorescent imaging, wherein different image sensors for fluorescent imaging may be paired with different filters to permit passage of different ranges of fluorescent emissions, wherein each range is configured to capture a particular characteristic of a target (e.g., vasculature or microvasculature, collagen, elastin, blood, bone, bacteria, malignancy, healthy or diseased cartilage, ligaments, tendons, connective tissue, lymphatics, nerve, muscle etc.).

The optical housing portion 140 can also include one or more excitation light sources. An excitation light source may provide a single wavelength of excitation light, chosen to excite tissue autofluorescence emissions and as well as fluorescence emissions of induced porphyrins in tumor/cancer cells. Additionally or alternatively, an excitation light source may provide a wavelength of excitation light chosen to excite bacterial autofluorescence emissions and/or exogenous fluorescence emissions of one or more of tissue and bacteria in a wound. In one example, the excitation light may have wavelengths in the range of about 350 nm –about 600 nm, or 350 nm – about 450 nm and 550 nm – about 600 nm, or, for example 405 nm, or for example 572 nm.

Alternatively, the excitation light source may be configured to provide two or more wavelengths of excitation light. The wavelengths of the excitation light may be chosen for different purposes, as will be understood by those of skill in the art. For example, by varying the wavelength of the excitation light, it is possible to vary the depth to which the excitation light penetrates a surface of a target such as a surgical bed or a wound. As depth of penetration increases with a corresponding increase in wavelength, it is possible to use different wavelengths of light to excite tissue below the surface of the target surface. In one example, excitation light having wavelengths in the range of 350 nm - 450 nm, for example 405 nm, and excitation light having wavelengths in the range of 550 nm to 600 nm, for example 572 nm, may penetrate target tissue to different depths, for example, about 500 μm – about 1 mm and about 2.5 mm, respectively. This will allow the user of the device, for example a doctor, a surgeon, or a pathologist, to visual tissue cells at the surface of the target and the subsurface of the target. Additionally or alternatively, an excitation light having a wavelength in the near infrared/infrared range may be used, for example excitation light having a wavelength of between about 750 nm and about 800 nm, for example 760 nm or 780 nm, may be used. In addition, to penetrating the tissue to a deeper level, use of this type of light source may be used in conjunction with a second type of imaging/contrast agent, such as for example infrared dye (e.g., IRDye 800, ICG). This will enable, for example, visualization of vascularization, vascular perfusion, and blood pooling in the target tissue. In addition, the utility of visualizing vascular perfusion be to improve anastomosis during reconstruction or to observe healing of the wound.

The imaging system 100 may include additional light sources, such as a white light source for white light (WL) imaging of the target. When required, the white light source can illuminate the target for primary and secondary image capture, as well as provide WL images as anatomical context for other images, such as fluorescent images. The white light source may include one or more white light LEDs. Other sources of white light may be used, as appropriate. As will be understood by those of ordinary skill in the art, white light sources should be stable and reliable, and not produce excessive heat during prolonged use.

The base body portion 110 of the imaging system 100 may include controls to initiate image capture and to permit switching/toggling between white light imaging and fluorescence imaging. The controls may also enable use of various excitation light sources together or separately, in various combinations, and/or sequentially. The controls may cycle through a variety of different light source combinations, may sequentially control the light sources, may strobe the light sources or otherwise control timing and duration of light source use. The controls may be automatic, manual, or a combination thereof, as will be understood by those of ordinary skill in the art. As discussed above, the touchscreen display 120 of base body portion 110 may function as a user interface to allow control of the imaging system 100. Alternatively, it is contemplated that separate controls, such as hand-actuated controls, for example buttons, may be used instead of or in addition to touchscreen controls. Such hand-actuated controls may be positioned, for example, on the handgrips 130 to allow the user to easily actuate the controls while holding and using the imaging system.

The optical housing portion 140 of the imaging system 100 may also contain one or more optical imaging filters configured to prevent passage of reflected excitation light to the camera image sensor(s). In one example, optical imaging filters can also be configured to permit passage of emissions having wavelengths corresponding to autofluorescence emissions of tissue cells and fluorescence emissions of the induced porphyrins in tissue cells. In another example, the system 100 may contain one or more optical imaging filters configured to permit passage of emissions corresponding to autofluorescence emissions of bacteria contained in the target as well exogenous fluorescence emissions of bacteria due to the use of contrast agents on the target surface. The imaging system 100 may also include filters configured to capture fluorescence and autofluorescence of both bacteria and tissues.

These optical filters may be selected to detect specific optical signals from the target/tissue/wound surface based on the wavelength of light desired. Spectral filtering of the detected optical signal(s) (e.g., absorption, fluorescence, reflectance) may also be achieved, for example, using a liquid crystal tunable filter (LCTF), or an acousto-optic tunable filter (AOTF) which is a solid-state electronically tunable spectral band-pass filter. Spectral filtering may also involve the use of continuous variable filters, and/or manual band-pass optical filters. These filters/filtering mechanisms may be placed in front of the imaging camera sensor to produce multispectral, hyperspectral, and/or wavelength-selective imaging of tissues.

The imaging system 100 may be modified by using optical or variably-oriented polarization filters (e.g., linear or circular combined with the use of optical wave plates) attached in a reasonable manner to the excitation/illumination light sources and an imaging sensor. In this way, the imaging system 100 may be used to image the target with polarized light illumination and non-polarized light detection or vice versa, or polarized light illumination and polarized light detection, with either white light reflectance and/or fluorescence imaging. This may permit imaging of wounds with minimized specular reflections (e.g., glare from white light imaging), as well as enable imaging of fluorescence polarization and/or anisotropy-dependent changes in connective tissues (e.g., collagens and elastin) within the wound and surrounding normal tissues. This may yield useful information about the spatial orientation and organization of connective tissue fibers associated with wound remodeling during healing [Yasui et al., (2004) Appl. Opt. 43: 2861-2867].

In one example embodiment, as shown in FIG. 6, the imaging system 100 may include three camera image sensors 102, 112, 107 and each sensor includes a fixed filter 161, 166, 171. For example, first and second white light sensors may be provided, each configured to receive visible light signals via a dedicated filter fixed to the respective sensor. Additionally, a sensor for fluorescent imaging may be configured to allow various desirable emission wavelengths to pass through to the fluorescent camera sensor. As previously discussed, different optical housing portions may contain different configurations of sensors, filters, and light sources which together are configured to create images of specific characteristics of a target.

FIG. 6 shows an exploded view of the optical housing 140 of the imaging system 100. As shown in FIG. 6, base body portion 110 may include a heat sink 160 positioned behind a heat sink 150 of the optical housing 140. The optical housing 140 may further include the three camera sensors 102, 112, 107, a printed circuit board (PCB) 173, an outer heat sink gasket 152, a camera shroud 144, three optical filters 161, 166, 171, a light diffuser for the white light source, an inner gasket/filter retainer 174, windows 175a, 175b, 175c, adhesive tape 176 (or other means for fixing the windows), and a lens assembly tip 180, which may include a feature to permit attachment of accessories.

As will be understood by those of skill in the art, the arrangement of the components in the optical housing of the imaging system may take on many configurations. Such configurations may be driven by size of the system, the footprint of the system, and the number of components used. However, when arranging the components, functional factors should also be considered. For example, issues such as light leakage from light sources of the system and/or an ambient light entering the optical housing may interfere with proper or optimal operation of the system, and may for example cause a less desirable output, such as image artifacts. The arrangement illustrated in FIG. 6 is an arrangement in which camera sensors are isolated so as to prevent light leakage from light sources and ambient light.

Figure 17:
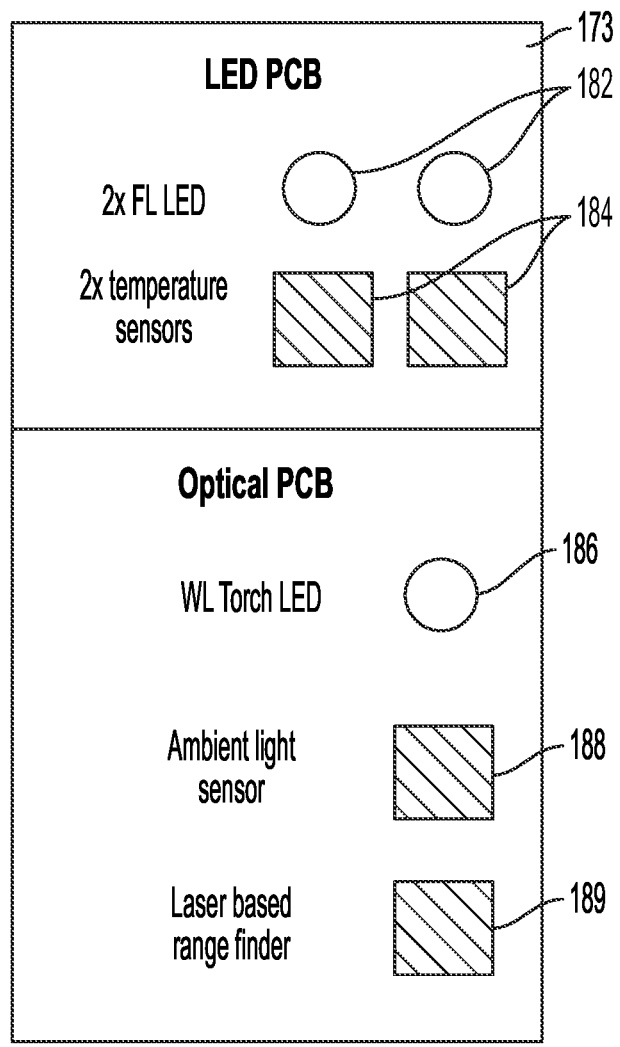
FIG. 17 is an example embodiment of a printed circuit board for use in an imaging system in accordance with one aspect of the present disclosure.

An example PCB 173 is shown in FIG. 17. As illustrated, the PCB 173 may include an excitation light source 182, such as for example two fluorescent LEDs, for example violet/blue LEDs having a wavelength of between about 400 nm –about 450 nm, and in one example, having a wavelength of about 405 nm ± 10 nm. In this embodiment, with reference to FIG. 2, the two violet/blue LEDs may be positioned, for example, on opposite sides of a longitudinal axis A of the housing 140, wherein the longitudinal axis A passes through a top and a bottom of the housing 140.

Additional LEDs having the same wavelength may be provided or only one LED may be used. Additionally, it is contemplated that additional excitation light sources having different wavelengths may be provided. PCB 173 may also include two temperature sensors 184, a white light or torch LED 186 to provide white light for white light imaging, an ambient light sensor 188, and optionally a range finder 189 (e.g., a laser-based range finder), which may be used as a backup to or in addition to the contactless wound measurement system disclosed herein.

In this manner, the system 100 may be designed to detect all or a majority of tissue autofluorescence (AF). For example, using a multi-spectral band filter, the device may image tissue autofluorescence emanating from the following tissue biomolecules, as well as blood-associated optical absorption, for example under 405 nm excitation: collagen (Types I, II, III, IV, V and others) which appear green, elastin which appears greenish-yellow-orange, reduced nicotinamide adenine dinucleotide (NADH), flavin adenine dinucleotide (FAD), which emit a blue-green autofluorescence signal, and bacteria/microorganisms, most of which appear to have a broad (e.g., green and red) autofluorescence emission.

Image analysis may further include calculating a ratio of red-to-green AF in the image. Intensity calculations may be obtained from regions of interest within the wound images. Pseudo-colored images may be mapped onto the white light images of the wound.

The system 100 may further map biodistribution of bacteria within the wound site and on the surrounding skin and thus may aid in targeting specific tissue areas requiring swabbing or biopsy for microbiological testing. Furthermore, using the imaging system 100 may permit the monitoring of the response of the bacterially-infected tissues to a variety of medical treatments, including the use of antibiotics and other therapies, such as photodynamic therapy (PDT), hyperbaric oxygen therapy (HOT), low level light therapy, or anti-Matrix Metalloproteinase (MMP). The system 100 may be useful for visualization of bacterial biodistribution at the surface as well as within the tissue depth of the wound, and also for surrounding normal tissues. The system 100 may thus be useful for indicating the spatial distribution of an infection. In general, the imaging system 100 may, therefore, be used to image and/or monitor targets such as a skin target, a tumor target, a wound target, a confined anatomical space or cavity, an oral target, an ear-nose-throat target, an ocular target, a genital target, an anal target, and any other suitable targets on a subject. For example, when the system 100 is held above a target tissue surface (e.g., a wound) to be imaged, the illuminating light sources may shine a narrow-bandwidth or broad-bandwidth violet/blue wavelength or other wavelength or wavelength band of light onto the tissue/wound surface thereby producing a flat and homogeneous field of light within the region-of-interest. The light also illuminates or excites the tissue down to a certain shallow depth. This excitation/illumination light interacts with the normal and diseased tissues and may cause an optical signal (e.g., absorption, fluorescence and/or reflectance) to be generated within the target tissue, which is subsequently captured by one of the camera image sensors.

By changing the excitation and emission wavelengths accordingly, the imaging system 100 may interrogate tissue components of the target (e.g., connective tissues and bacteria in a wound) at the surface and at certain depths within the target tissue (e.g., a wound). For example, by changing from violet/blue (~400-500 nm) to green (~500-540 nm) wavelength light, excitation of deeper tissue/bacterial fluorescent sources may be achieved, for example in a wound. Similarly, by detecting longer wavelengths, fluorescence emission from tissue and/or bacterial sources deeper in the tissue may be detected at the tissue surface. For wound assessment, the ability to interrogate surface and/or sub-surface fluorescence may be useful, for example in detection and potential identification of bacterial contamination, colonization, critical colonization and/or infection, which may occur at the surface as well as at depth within a wound (e.g., in chronic non-healing wounds).

The imaging system 100 may also include a wireless module and be configured for completely wireless operation. It may utilize a high throughput wireless signal and have the ability to transmit high-definition video with minimal latency. The system may be both Wi-Fi and Bluetooth enabled – Wi-Fi for data transmission, Bluetooth for quick connection. The system may utilize a 5 GHz wireless transmission band operation for isolation from other devices. Further, the system may be capable of running as soft access point, which eliminates the need for a connection to the internet and keeps the device and module connected in isolation from other devices which is relevant to patient data security. The system may be configured for wireless charging and include inductive charging coils. Additionally or alternatively, the system may include a port configured to receive a charging connection.

As above, other supporting electronic systems and components of the electronics system utilized by the system 100 can include memory, such as a flash memory device, a rechargeable battery such as a lithium-ion battery, and an inductive battery charging system. Some components of the electronics system can include communications components, such as Wi-Fi and/or Bluetooth radio subsystem, and spatial orientation components such as one or more of magnetometers, accelerometers, and gyroscopes. Furthermore, the electronics system can include various user controls, such as a power switch, system status LEDs, charging status LEDs, a picture capture switch, video capture switch, and imaging mode switch. The various user controls can interface with the other components of the electronics system through a user interface module that provides signals to and from the user controls.

Other components in the electronic system can include drivers for the fluorescent, infrared, and white light LEDs, a USB hub for uplink or downlink data signals and/or power supply from an external computer system to which the electronic system can be connected through the USB hub, such as a workstation or other computer. The electronics system can also include one or more devices that provide feedback to a user, such as, without limitation, a speaker. Other feedback devices could include various auditory and visual indicators, haptic feedback devices, displays, and other devices.

Figure 19:
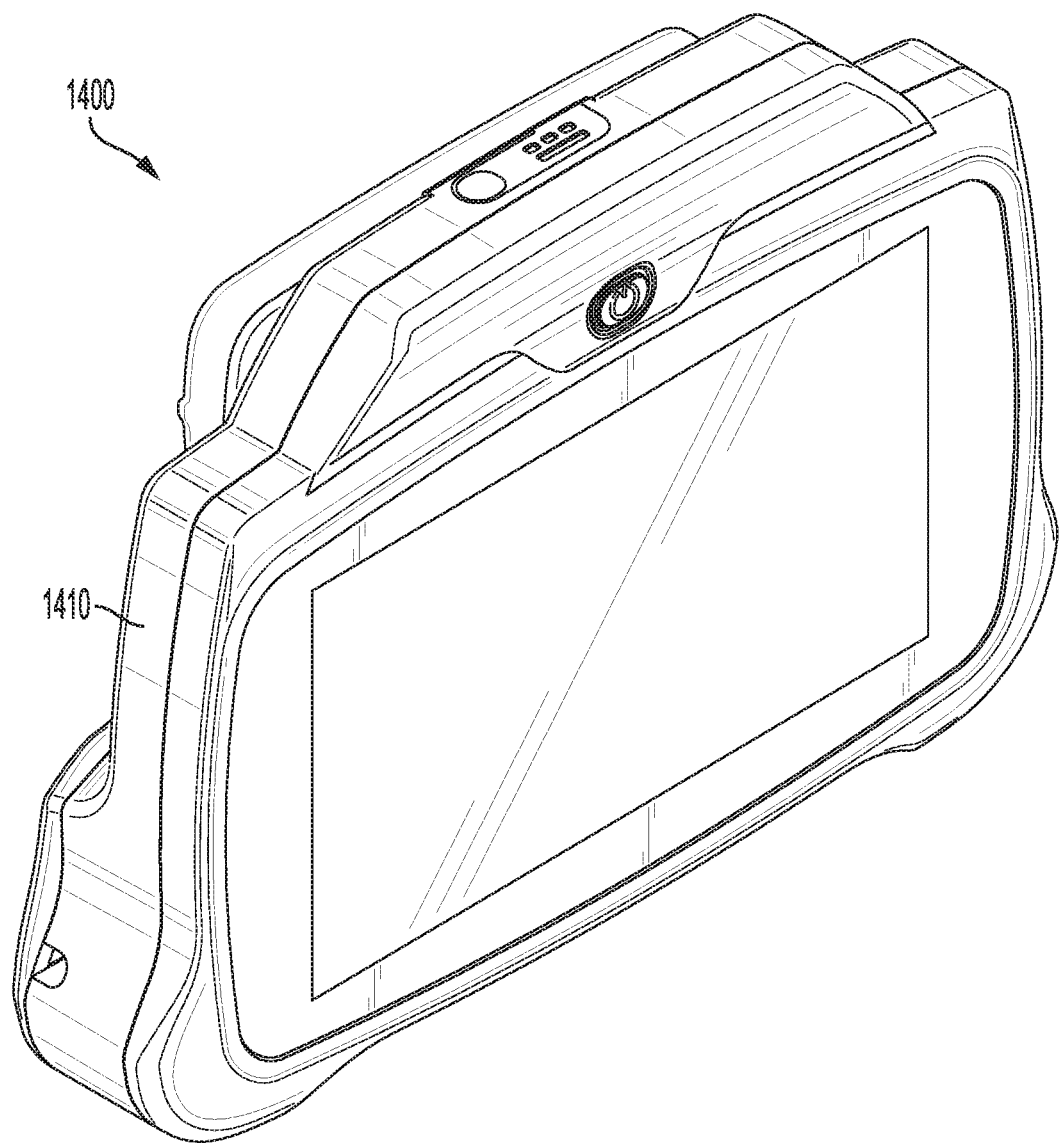
FIG. 19 is a front view of another embodiment of a handheld imaging system according to the present disclosure.
Figure 20:
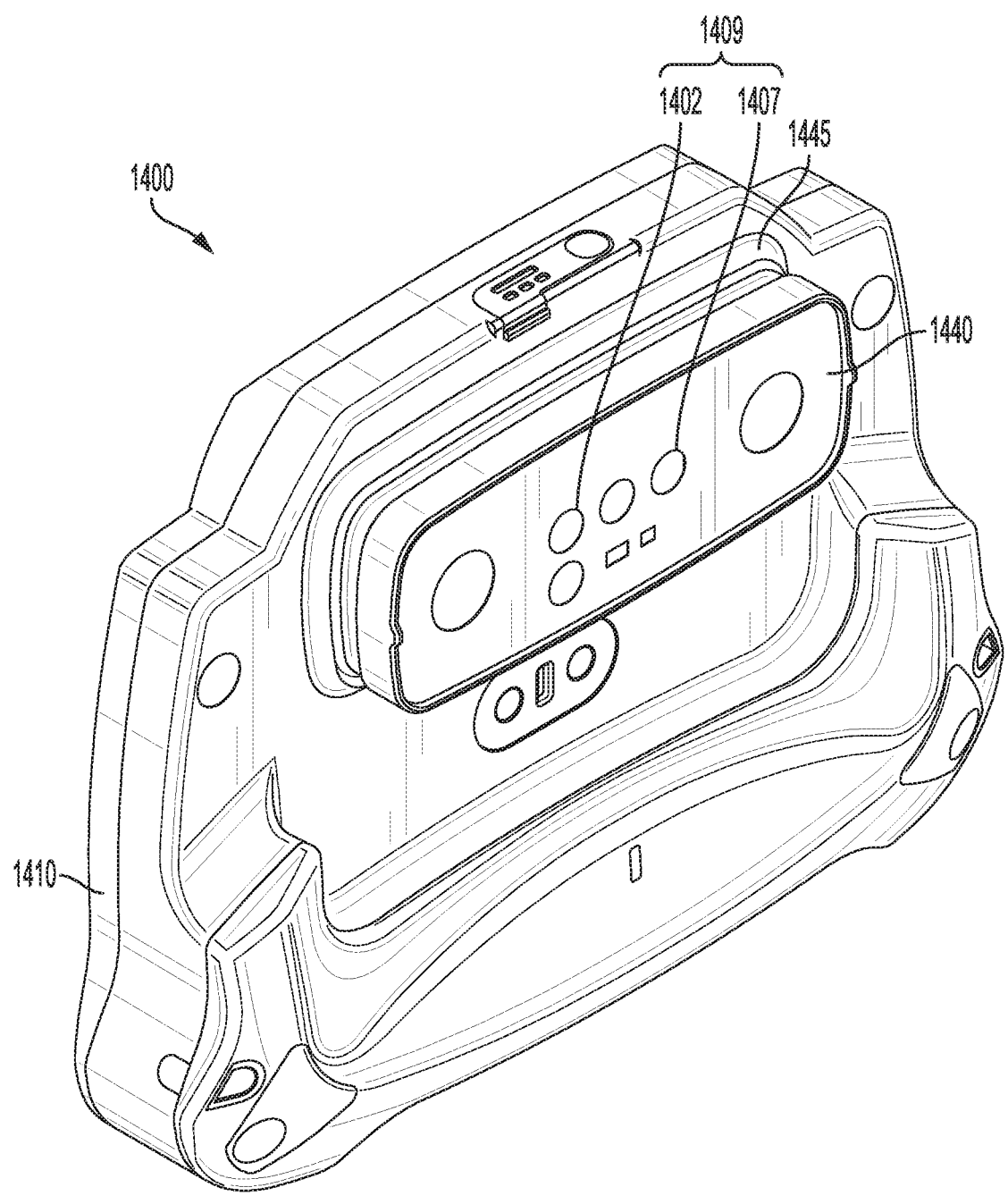
FIG. 20 is a back view of the handheld imaging system of FIG. 19.

Those of ordinary skill in the art will understand that the wound imaging system 100 as described above and illustrated with reference to FIGS. 1-7 is exemplary only, and that any wound imaging system with stereoscopic imaging capabilities may utilize the systems and methods of the present disclosure. FIGS. 19 and 20, for example, illustrate another exemplary embodiment of an imaging system 1400 in accordance with the present disclosure. Like the system 100, system 1400 is a portable, handheld wound imaging system, which utilizes various combinations of white light (WL) imaging, fluorescence (FL) imaging, infrared (IR) imaging, thermal imaging, and/or three-dimensional mapping. The imaging system 1400 comprises a base body portion 1410, which houses the processor, and an optical portion 1440, which houses a stereoscopic camera assembly 1409. Similar to the system 100, the optical housing portion 1440 may be detachable from the base body portion 1410, such that the optical housing portion 1440, illustrated in FIG. 19 as a rectangular housing, is configured to be received in a corresponding rectangular opening 1445 on the base body portion 1410. The optical components, including a primary camera sensor 1402 and a secondary camera sensor 1407, are arranged in a generally linear manner across a width of the optical housing 1440, as discussed above with reference to FIG. 2.

Furthermore, although the disclosed systems and methods for measurement without fiducial elements, markers or other artificial fixed reference points are disclosed for use with wound monitoring and analysis, such as, for example, using the wound imaging systems 100 and 1400 as described above and illustrated with reference to FIGS. 1-7 and 19-20, those of ordinary skill in the art will understand that systems 100 and 1400 are exemplary only, and that the disclosed systems and methods may be utilized in various devices, systems, and/or methods and in various applications to measure a target (i.e., without placing fiducials in the field of view or touching the target and/or an area around the target) using a stereoscopic imaging device. Such devices and methods may include cameras used in operating theaters, i.e., used during surgery, either in-person surgery or remotely-controlled surgical procedures. Further, the method can be used outside of medical environments, in places where stereoscopic camera systems are used and measurements of a target are required.

Various embodiments of the present disclosure contemplate, for example, utilizing the disclosed measurement methods in any medical device with stereoscopic imaging capabilities, including, for example, various endoscopic and laparoscopic devices, utilizing stereoscopic imaging modalities, such as, for example, The PINPOINT endoscopic fluorescence imaging camera manufactured by Stryker. The present disclosure further contemplates adapting existing imaging devices, including existing wound imaging devices, endoscopes, and laparoscopes, which have stereoscopic cameras to utilize the methods disclosed herein.

A method of adapting a portable, handheld system having first and second camera sensors may include, for example, storing instructions in a non-transitory computer-readable medium associated with a processor of the portable, handheld system, such that, when executed by the processor, the portable, handheld imaging system performs operations comprising the method 200 of FIG. 8.

Other exemplary uses for such systems may include:
Clinically- and research-based imaging of small and large (e.g., veterinary) animals.
Detection and monitoring of contamination (e.g., bacterial contamination) in food/animal product preparation in the meat, poultry, dairy, fish, agricultural industries.
Detection of 'surface contamination' (e.g., bacterial or biological contamination) in public (e.g., health care) and private settings.
Multi-spectral imaging and detection of cancers in human and/or veterinary patients.
As a research tool for multi-spectral imaging and monitoring of cancers in experimental animal models of human diseases (e.g., wound and cancers).
Forensic detection, for example of latent fingerprints and biological fluids on non-biological surfaces.
Imaging and monitoring of dental plaques, carries and cancers in the oral cavity.
Imaging and monitoring device in clinical microbiology laboratories.
Testing anti-bacterial (e.g., antibiotic), disinfectant agents.

In all such applications, as discussed above in detail, the system may generally comprise: i) an imaging device having a primary camera sensor and a secondary camera sensor and ii) a processor configured to determine a parallax value for a target from images of the target captured by the camera sensors, wherein the parallax value is used to compute measurement data related to the target. The system may also have iii) one or more excitation/illumination light sources and iv) one or more camera sensors which may be combined with one or more optical emission filters, or spectral filtering mechanisms.

Such systems can, for example, include software allowing a user to control the system, including control of imaging parameters, visualization of images, storage of image data and user information, transfer of images and/or associated data, and/or relevant image analysis (e.g., diagnostic algorithms). The systems can further include software for measuring the imaged target (i.e., utilizing the computed parallax value), calculating quantities of various items found in the imaged target. For example, if the target is a wound, the systems can include software configured to calculate wound size, wound depth, wound perimeter, wound area, wound volume, identify various types of tissues within the wound (collagen, elastic, vasculature) and the percentages of each within the wound. Further, the systems can determine an amount or quantity of bacteria in the wound, the bacterial load, distinguish between various types of bacteria within the load and identify relative percentages. As above, examples of suitable software and methods are described, for example, in U.S. Pat. No. 2020/0364862, the entire content of which is incorporated by reference herein.

The systems may be configured to co-register white light images, fluorescent images, thermal images, and other images of the target. The systems may be configured to create three-dimensional maps of the target. The systems may be configured to enhance color distinctions between different tissue types identified in an image. The systems may be configured to determine tissue classification of the target based on different colors or image features captured in the fluorescent image. The systems may be configured to delineate between diseased and healthy tissues therein providing a map for users to selectively remove diseased tissues while sparing surrounding healthy tissues is a targeted manner.

Various types of filters, power sources, light sources, excitation light sources, camera sensors, and charging configurations may be present in the presently disclosed systems. In various embodiments, for example, the imaging systems and methods disclosed herein may rely on tissue autofluorescence and bacterial autofluorescence, as well as autofluorescence of other targeted materials. Additionally or alternatively, the present application further contemplates the use of exogenous contrast agents which may be applied topically, ingested, or otherwise applied. Examples of such components and agents for imaging a target are described, for example, in U.S. Pat. No. 9,042,967, which is a national stage application of PCT/CA2009/000680, filed internationally on May 20, 2009, which claims benefit to U.S. Provisional Application No. 61/054,780, filed May 20, 2008, the entire content of each of which is incorporated by reference herein.

The systems interface ports may support both wired (e.g., USB) or wireless (e.g., Bluetooth, WiFi, and similar modalities) data transfer or $3^{rd}$ party add-on modules to a variety of external devices, such as: a head-mounted display, an external printer, a tablet computer, laptop computer, personal desk top computer, a wireless device to permit transfer of imaging data to a remote site/other device, a global positioning system (GPS) device, a device allowing the use of extra memory, and a microphone.

The systems may be used to guide debridement of wounds, to identify types of bacteria to assist in determination of appropriate treatments/drugs/antibiotics.

The systems may also be attached to a mounting mechanism (e.g., a tripod or stand) for use as a relatively stationary optical imaging device for white light, fluorescence and reflectance imaging of objects, materials, and surfaces (e.g., a body). This may allow the device to be used on a desk or table or for 'assembly line' imaging of objects, materials and surfaces. In some embodiments, the mounting mechanism may be mobile.

Other features of the disclosed systems may include the capability of digital image and video recording, with audio, methods for documentation (e.g., with image storage and analysis software), and wired or wireless data transmission for remote telemedicine/E-health needs.

In addition to providing detecting of bacterial strains, the systems may be used for differentiating the presence and/or location of different bacterial strains (e.g., Staphylococcus aureus or Pseudomonas aeruginosa), for example in wounds and surrounding tissues. This may be based on the different autofluorescence emission signatures of different bacterial strains, including those within the 490-550 nm and 610-640 nm emission wavelength bands when excited by violet/blue light, such as light around 405 nm. Other combinations of wavelengths may be used to distinguish between other species on the images. This information may be used to select appropriate treatment, such as choice of antibiotic.

The systems may be scanned above any wound (e.g., on the body surface) such that the excitation light may illuminate the wound area. The wound may then be inspected using the system such that the operator may view the wound in real-time, for example, via a viewer on the imaging system or via an external display device (e.g., heads-up display, a television display, a computer monitor, LCD projector or a head-mounted display). It may also be possible to transmit the images obtained from the systems in real-time (e.g., via wireless communication) to a remote viewing site, for example for telemedicine purposes, or send the images directly to a printer or a computer memory storage. Imaging may be performed within the routine clinical assessment of patient with a wound.

It will be appreciated by those ordinarily skilled in the art having the benefit of this disclosure that the present disclosure provides various exemplary devices, systems, and methods for contactless measurement of a target, as used, for example, in wound measurement and in other clinical applications, such as, for example, the intraoperative and/or in vitro visualization of tumors and/or residual cancer cells on surgical margins. Further modifications and alternative embodiments of various aspects of the present disclosure will be apparent to those skilled in the art in view of this description.

Furthermore, the systems and methods may include additional components or steps that were omitted from the drawings for clarity of illustration and/or operation. Accordingly, this description is to be construed as illustrative only and is for the purpose of teaching those skilled in the art the general manner of carrying out the present disclosure. It is to be understood that the various embodiments shown and described herein are to be taken as exemplary. Elements and materials, and arrangements of those elements and materials, may be substituted for those illustrated and described herein, parts and processes may be reversed, and certain features of the present disclosure may be utilized independently, all as would be apparent to one skilled in the art after having the benefit of the description herein. Changes may be made in the elements described herein without departing from the spirit and scope of the present disclosure and following claims, including their equivalents.

It is to be understood that the particular examples and embodiments set forth herein are non-limiting, and modifications to structure, dimensions, materials, and methodologies may be made without departing from the scope of the present disclosure.

Furthermore, this description's terminology is not intended to limit the present disclosure. For example, spatially relative terms—such as "beneath," "below," "lower," "above," "upper," "bottom," "right," "left," "proximal," "distal," "front," and the like-may be used to describe one elements or feature's relationship to another element or feature as illustrated in the figures. These spatially relative terms are intended to encompass different positions (i.e., locations) and orientations (i.e., rotational placements) of a device in use or operation in addition to the position and orientation shown in the drawings.

For the purposes of this specification and appended claims, unless otherwise indicated, all numbers expressing quantities, percentages or proportions, and other numerical values used in the specification and claims, are to be understood as being modified in all instances by the term "about" if they are not already. Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the present disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

It should be understood that while the present disclosure has been described in detail with respect to various exemplary embodiments thereof, it should not be considered limited to such, as numerous modifications are possible without departing from the broad scope of the appended claims, including the equivalents they encompass.

We claim:

1. A portable, handheld imaging system for measurement of a target, comprising:
    an imaging assembly comprising a first camera sensor and a second camera sensor, the first camera sensor being separated from the second camera sensor by a fixed separation distance; and
    a processor operably coupled to the imaging assembly, the processor being configured to:
        calibrate the imaging assembly by capturing calibration images with the imaging assembly and calculating manufacturing coefficients from the captured calibration images;
        store the calculated manufacturing coefficients in a reference table;
        activate the imaging assembly to capture a primary image of the target with the first camera sensor and to capture a secondary image of the target with the second camera sensor, wherein the target is in a field of view of each of the first and second camera sensors;
        analyze the captured primary and secondary images to determine a pixel shift value for the target;
        calculate a parallax value between the primary image and the secondary image by determining a target-plane pixel size in mm based on the stored manufacturing coefficients and the determined pixel shift value;
        compute measurement data related to the target based on the calculated parallax value; and
        output the measurement data to a display of the handheld imaging system.

2. The system of claim 1, wherein the imaging assembly is a stereoscopic imaging assembly and the first and second camera sensors are aligned along a plane transverse to a longitudinal axis of the stereoscopic imaging assembly and are positioned on opposite sides of the longitudinal axis, wherein the longitudinal axis passes through a top and a bottom of the handheld imaging device.

3. The system of claim 1, wherein the fixed separation distance is at least about 1 mm.

4. The system of claim 1, wherein a field of view of at least one of the first and second camera sensors is offset such that the secondary image overlaps the primary image.

5. The system of claim 4, wherein the field of view of the second camera sensor is offset such that the secondary image is shifted horizontally by a predetermined, fixed pixel count.

6. The system of claim 1, wherein analyzing the captured primary and secondary images comprises shifting the secondary image until it exactly overlaps the primary image.

7. The system of claim 1, wherein the processor is configured to use the pixel size to compute the measurement data.

8. The system of claim 1, wherein the measurement data comprises one or more of a size, an area, a three-dimensional surface, and/or a depth of the target.

9. The system of claim 1, wherein the target is a wound in tissue and the measurement data comprises one or more of a size, an area, a three-dimensional surface, and/or a depth of the wound.

10. The system of claim 1 further comprising:
at least one excitation light source configured to emit excitation light during fluorescent imaging;
a third camera sensor;
a first filter configured to detect and permit passage of optical signals, responsive to illumination of the target with the excitation light and having a wavelength corresponding to one or more of bacterial fluorescence, bacterial autofluorescence, tissue fluorescence, and tissue autofluorescence, to the third camera sensor;
a white light source configured to emit white light during white light imaging; and
a second filter configured to detect and permit passage of optical signals, responsive to illumination of the target with the white light and having a wavelength in a visible light range, to one of the first and second camera sensors of the imaging assembly,
wherein the processor is configured to receive the detected fluorescent and white light optical signals and to output a representation of the target to the display based on the detected optical signals.

11. The system of claim 10, wherein the at least one excitation light source comprises at least one violet/blue LED configured to emit light having a wavelength of 405 nm ± 10 nm.

12. The system of claim 10, further comprising a housing, the display being positioned on a front side of the housing and the at least one excitation light source being positioned on a rear side of the housing.

13. The system of claim 12, wherein the at least one excitation light source includes first and second violet/blue LEDs, each LED configured to emit light having a wavelength of 405 nm ± 10 nm, wherein the first and second violet/blue LEDs are positioned on opposite sides of a longitudinal axis of the housing, wherein the longitudinal axis passes through a top and a bottom of the housing.

14. The system of claim 12, wherein the housing is a modular housing comprising a display unit and an optical unit, the handheld imaging device, the excitation light source, and the first and second filters being contained in the optical unit.

15. The system of claim 14, wherein the optical unit is releasably attached to the display unit.

16. The system of claim 1, wherein the processor is configured to perform at least the operations of analyzing and calculating without using fiducial elements, markers or other artificial fixed references in the field of view of the first and/or second camera sensors.

17. The system of claim 1, wherein the primary and secondary images are selected from a group consisting of white light images, fluorescence images, and infrared images.

18. The system of claim 17, wherein the primary and secondary images are both white light images, both fluorescence images, or both infrared images.

19. A method for measurement of a target, the method comprising:
simultaneously capturing a primary image of the target and a secondary image of the target, wherein the primary image is captured by a first camera sensor of a handheld imaging system and the secondary image of the target is captured by a second camera sensor of the handheld imaging system;
on a display screen of the handheld imaging system, defining a contour region of the target within the captured primary image; and
with a processor of the handheld imaging system:
determining a pixel shift value for the target within the contour region by applying a parallax algorithm to shift the secondary image until it exactly overlaps the primary image,
calculating a parallax value of the primary image at a center of the contour region by applying a least-squares linear regression algorithm on the determined pixel shift value to calculate a mm per pixel dimension (Q) and a distance to the target (D),
computing measurement data related to the target based on the defined contour region and the calculated parallax value, and
outputting the measurement data to the display screen of the handheld imaging system.

20. The method of claim 19, wherein a field of view of the first and/or second camera sensors does not include fiducial elements, markers or other artificial fixed references.

21. The method of claim 19, wherein the target being imaged is within a field of view of both the first and the second camera sensors.

22. The method of claim 19, further comprising, prior to capturing the primary and secondary images, calibrating the handheld imaging system, wherein the calibrating comprises:
positioning the handheld imaging system in a calibration apparatus;
capturing calibration images of predefined target objects; and
calculating non-linear point coefficients from the captured calibration images to determine manufacturing coefficients for the handheld imaging system.

23. The method of claim 22, further comprising, prior to defining the contour region, applying the determined manufacturing coefficients to offset and rotate the secondary image.

24. The method of claim 22, wherein applying the least-squares linear regression algorithm on the determined pixel shift value comprises using the non-linear point coefficients.

25. The method of claim 19, wherein computing the measurement data comprises computing one or more of a size, an area, a three-dimensional surface, and/or a depth of the target.

26. The method of claim 19, wherein the target is a wound in tissue, and wherein computing measurement data comprises computing one or more of a size, an area, a three-dimensional surface, and/or a depth of the wound.

27. The method of claim 19, further comprising, prior to image capture by the handheld imaging system, determining, in real time, a distance from the primary camera sensor to the target by applying a parallax transform to preview images;

and preventing the image capture when the determined distance is outside a predefined range.

28. The method of claim 19, further comprising, prior to image capture by the handheld imaging system, detecting, in real time, whether the parallax value is stable or unstable based on the parallax algorithm; and preventing the image capture when the detected parallax value is unstable.

29. The method of claim 19, wherein defining the contour region includes prompting a user to trace a contour of a region of interest on the display screen of the handheld imaging system.

30. The method of claim 19, wherein defining the contour region includes automatically tracing a contour of the primary image and saving the contour as a series of two-dimensional points.

31. The method of claim 19, wherein defining the contour region comprises measuring multiple parallax regions of the target within the captured primary image to determine an angle between the handheld imaging system and a plane of the target.

32. The method of claim 19, wherein defining the contour region comprises measuring multiple parallax regions of the target within the captured primary image to determine a curvature of a surface of the target.

33. The method of claim 19, wherein simultaneously capturing primary and secondary images of the target comprises simultaneously capturing primary and secondary white-light images of the target.

34. The method of claim 19, wherein simultaneously capturing primary and secondary images of the target comprises simultaneously capturing primary and secondary fluorescence images of the target.

35. The method of claim 19, wherein simultaneously capturing primary and secondary images of the target comprises simultaneously capturing primary and secondary infrared images of the target.

36. The method of claim 19, further comprising:
   illuminating at least a portion of the target with at least one excitation light source of the handheld imaging system to cause one or more of a part, a component, and/or a biomarker of the illuminated portion of the target to fluoresce;
   filtering optical signals responsive to the illumination of the target with the at least one excitation light source, wherein filtering the optical signals includes preventing passage of reflected excitation light and permitting passage of optical signals having a wavelength corresponding to one or more of bacterial fluorescence, bacterial autofluorescence, tissue autofluorescence and exogenous tissue fluorescence through a fluorescent filter contained in the handheld imaging system;
   detecting the filtered optical signals with a fluorescent camera sensor of the handheld imaging system;
   co-registering data from the primary and/or secondary images with data based on the detected filtered optical signals; and
   displaying on the display of the handheld imaging system a composite image of the illuminated portion of the target, the composite image including measurements of the target and fluorescent representations of bacteria and/or tissue components present in the target.

37. A non-transitory computer-readable medium storing instructions that, when executed by a processor of a portable, handheld imaging system, cause the portable, handheld imaging system to perform operations comprising the method of claim 19.

38. A method of adapting a portable, handheld system having first and second camera sensors, the method comprising:
   storing instructions in a non-transitory computer-readable medium associated with a processor of the portable, handheld system, such that, when executed by the processor, the portable, handheld imaging system performs operations comprising the method of claim 19.

39. The system of claim 3, wherein the fixed separation distance is about 21 mm.

40. A method for measurement of a target, the method comprising:
   capturing calibration images with first and second camera sensors of a handheld imaging system and calculating manufacturing coefficients from the captured calibration images;
   storing the calculated manufacturing coefficients in a reference table within a processor of the handheld imaging system;
   simultaneously capturing a primary image of the target and a secondary image of the target, wherein the primary image is captured by the first camera sensor and the secondary image of the target is captured by the second camera sensor;
   on a display screen of the handheld imaging system, defining a contour region of the target within the captured primary image; and
   with the processor of the handheld imaging system:
      determining a pixel shift value for the target within the contour region by applying a parallax algorithm to shift the secondary image until it exactly overlaps the primary image,
      calculating a parallax value of the primary image at a center of the contour region by determining a target-plane pixel size in mm based on the stored manufacturing coefficients and the determined pixel shift value,
      computing measurement data related to the target based on the defined contour region and the calculated parallax value, and
      outputting the measurement data to the display screen of the handheld imaging system.

* * * * *